United States Patent
Kerschen et al.

(10) Patent No.: US 8,809,526 B2
(45) Date of Patent: Aug. 19, 2014

(54) SYNTHESIS OF CYCLOPENTAQUINAZOLINES

(75) Inventors: James Alan Kerschen, Somerset, NJ (US); Alexander James Bridges, Saline, MI (US); Sean Mark Dalziel, San Francisco, CA (US); Olivier Dapremont, Cameron Park, CA (US); Hyunjung Kim, Collegeville, PA (US); Andrew S. Thompson, Mountainside, NJ (US); James Robert Zeller, Scottsdale, AZ (US)

(73) Assignee: ONYX Pharmaceuticals, Inc., San Francisco, CA (US)

( * ) Notice: Subject to any disclaimer, the term of this patent is extended or adjusted under 35 U.S.C. 154(b) by 0 days.

(21) Appl. No.: 13/810,763

(22) PCT Filed: Jul. 15, 2011

(86) PCT No.: PCT/US2011/001235
§ 371 (c)(1),
(2), (4) Date: Mar. 25, 2013

(87) PCT Pub. No.: WO2012/011939
PCT Pub. Date: Jan. 26, 2012

(65) Prior Publication Data
US 2013/0211082 A1  Aug. 15, 2013

Related U.S. Application Data

(60) Provisional application No. 61/399,861, filed on Jul. 19, 2010.

(51) Int. Cl.
*C07D 455/00* (2006.01)
(52) U.S. Cl.
CPC .................... *C07D 455/00* (2013.01)
USPC ....................................... 544/249
(58) Field of Classification Search
CPC .................................................. C07D 455/00
USPC .......................... 544/224, 344, 249
See application file for complete search history.

(56) References Cited

U.S. PATENT DOCUMENTS

| 5,747,499 | A | * | 5/1998 | Bavetsias et al. | 514/267 |
| 6,699,861 | B1 |  | 3/2004 | Skelton et al. | |
| 7,250,511 | B2 | * | 7/2007 | Bavetsias | 544/344 |
| 7,250,611 | B2 |  | 7/2007 | Bavetsias | |
| 7,297,701 | B2 |  | 11/2007 | Bavetsias et al. | |
| 7,528,141 | B2 |  | 5/2009 | Bavetsias et al. | |
| 2005/0009851 | A1 |  | 1/2005 | Bavetsias et al. | |
| 2009/0023760 | A1 |  | 1/2009 | Bavetsias et al. | |

FOREIGN PATENT DOCUMENTS

| GB | 2272217 | 5/1994 |
| WO | 9411354 | 5/1994 |
| WO | 9530673 | 11/1995 |
| WO | 03020706 | 3/2003 |
| WO | 03020748 | 3/2003 |

OTHER PUBLICATIONS

Bavetsias, et al., Cyclopenta[g]quinazolinone-based inhibitors of thymidylate synthase targeting .alpha.-folate receptor overexpressing tumors: synthetic approaches to 4-{N-[(6RS)-2-hydroxymethyl-4-oxo-3,4,7,8-tetrahydro-6H-cyclopenta[g]quinazolin-6-yl]-N-(prop-2-ynyl)amino}benzoic acid, Tetrahedron, 63(7), 1537-1543 (2007).*
T. Green and P. Wuts, Protective Groups in Organic Synthesis, 4th Edition, John Wiley and Sons, 2006, 7 pages.
Smith, M.B., March's Advances Organic Chemistry, 5th Edition, J. Wiley Interscience, 2001, 2 pages.

* cited by examiner

*Primary Examiner* — Erich A Leeser
(74) *Attorney, Agent, or Firm* — Tarolli, Sundheim, Covell & Tummino LLP

(57) ABSTRACT

A method of producing 6-amino-cyclopenta[g]quinazolines, in enantiomerically enriched form, is provided. In particular, the method may be applicable to the synthesis of N—{N-{4-[N-((6S)-2 -hydroxymethyl-4-oxo-3,4,7,8-tetrahydro-6H-cyclo-penta[g]quinazolin-6-yl)-N-(prop-2 -ynyl)amino]benzoyl}-L-γ-glutamyl}-D-glutamic acid (ONX-0801).

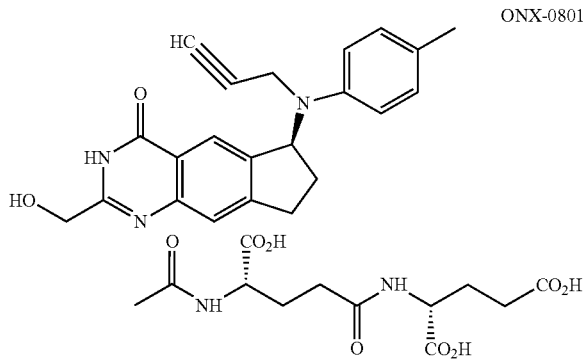

66 Claims, No Drawings

SYNTHESIS OF CYCLOPENTAQUINAZOLINES

CROSS-REFERENCE TO RELATED APPLICATIONS

This application is the U.S. national phase entry of PCT/US2011/001235, with an international filing date of Jul. 15, 2011, which claims priority from U.S. Provisional Application Ser. No. 61/399,861, filed Jul. 19, 2010, the entire contents of which are incorporated herein by reference.

TECHNICAL FIELD

The present invention relates to a new method for the synthesis of cyclopentaquinazolines. In particular, the invention concerns a method of producing 6-amino-cyclopenta[g]quinazolines, in enantiomerically enriched form.

BACKGROUND

A number of patents and publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

Cyclopentaquinazoline Compounds and Methods of Synthesis

WO 94/11354 describes tricyclic compounds, having a cyclopenta[g]quinazoline core, which are of general formula (I)

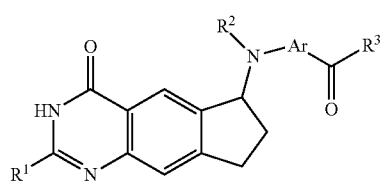

wherein $R^1$ is hydrogen, amino, $C_{1-4}$alkyl, $C_{1-4}$alkoxy, hydroxy-$C_{1-4}$alkyl or fluoro-$C_{1-4}$alkyl;

$R^2$ is hydrogen, $C_{1-4}$alkyl, $C_{3-4}$alkenyl, $C_{3-4}$alkynyl, hydroxy-$C_{2-4}$alkyl, halogeno-$C_{2-4}$alkyl or cyano-$C_{1-4}$alkyl;

Ar is phenylene, thiophenediyl, thiazolediyl, pyridinediyl or pyrimidinediyl, which may optionally bear one or two substituents selected from the group consisting of halogen, hydroxy, amino, nitro, cyano, trifluoromethyl, $C_{1-4}$alkyl and $C_{1-4}$alkoxy; and $R^3$ is a group of formula —NHCH($CO_2$H)-$A^1$-$Y^1$ wherein $A^1$ is $C_{1-6}$alkylene and $Y^1$ is carboxy, tetrazol-5-yl, N—[$C_{1-4}$ alkylsulfonyl]carbamoyl, N-(phenylsulfonyl)carbamoyl, tetrazol-5-ylthio, tetrazol-5-ylsulfinyl or tetrazol-5-ylsulfonyl, wherein said N-(phenylsulfonyl)carbamoyl group may optionally bear one or two substituents on the phenyl ring selected from halogeno, nitro, $C_{1-4}$alkyl and $C_{1-4}$alkoxy, or $Y^1$ is a group of the formula —CONH—CH($CO_2$H)-$A^2$-$Y^2$ wherein the α-amino acid carbon atom has the D-configuration, $A^2$ is $C_{1-6}$alkylene and $Y^2$ is carboxy or tetrazol-5-yl, or $R^3$ is a N-linked naturally-occurring amino acid selected from the group consisting of L-alanine, L-leucine, L-isoleucine, L-valine and L-phenylalanine, or $R^3$ is a group of the formula —NH-$A^3$-$Y^3$ wherein $A^3$ is $C_{1-3}$alkylene and $Y^3$ is phenyl which may optionally bear one, two or three substituents selected from the group consisting of halogeno, hydroxy, amino, nitro, cyano, trifluoromethyl, $C_{1-4}$alkyl and $C_{1-4}$alkoxy.

In WO 94/11354 the synthesis of compounds of formula I is described and may involve reacting an acid of formula (II), where $R^4$ is hydrogen or a protecting group, or a reactive derivative thereof, with an appropriate amine $R^3$—H.

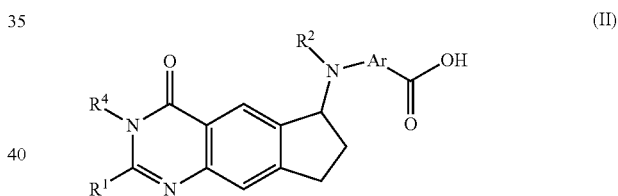

Preparation of the acids of formula (II) themselves, by standard procedures, is also described, for example by reaction of a compound of formula (III), where Z is a displaceable group, with an amine of formula HN$R^2$—Ar—$CO_2R^5$ where $R^5$ is a carboxylic acid protecting group which can be removed after the coupling to produce compound (II).

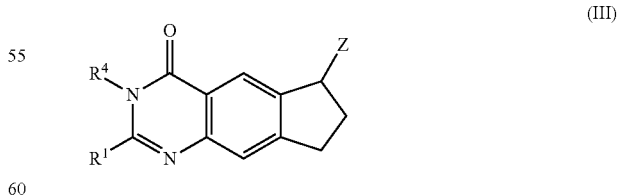

The displacements on (III) which are exemplified in WO 94/11354 all involve displacement with compounds of formula $H_2$N—Ar—$CO_2R^5$ to form intermediates of formula (IV), which are subsequently alkylated on the C6-nitrogen to form compounds of formula (II).

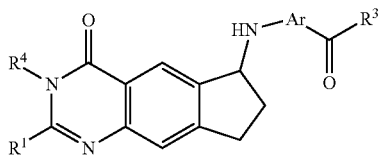

(IV)

A method of resolving compounds of general formula (II) to obtain the more active (6S)-enantiomers is also revealed in WO 94/11354. This method involves taking racemic acids of formula (II) and condensing them with a chiral amino acid, preferably L-glutamic acid, or (S)-2-aminoadipic acid to form an amide of formula (V) as a 1:1 mixture of diastereoisomers.

Use of an appropriate protease, such as Carboxypeptidase $G_2$ selectively hydrolyzes the 6S-diastereoisomer, allowing for a straightforward separation of 6S-(II) from the 6R-(V).

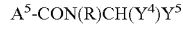

(V)

This method of resolution is lengthy, as the amide has to be made with an ester of the amino acid, which is subsequently hydrolyzed to an acid of formula (V). Moreover, the enzymatic hydrolysis requires large quantities of the enzyme, and may not be technically or economically feasible to scale up to produce commercial quantities of compounds of formula (I).

Further compounds, of general formula (VI) are disclosed in WO 95/30673

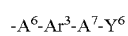

(VI)

wherein $R^1$ is hydrogen, amino, $C_{1-4}$alkyl, $C_{1-4}$alkoxy, $C_{1-4}$hydroxyalkyl or $C_{2-4}$-fluoroalkyl;
wherein $R^2$ is hydrogen, amino, $C_{1-4}$alkyl, $C_{3-4}$alkenyl, $C_{2-4}$hydroxyalkyl, $C_{2-4}$halogenoalkyl or $C_{1-4}$cyanoalkyl;
$Ar^1$ is phenylene, thiophenediyl, thiazolediyl, pyridinediyl or pyrimidinediyl which may optionally bear one or two substituents selected from halogeno, hydroxy, amino, nitro, cyano, trifluoromethyl, $C_{1-4}$alkyl, and $C_{1-4}$alkoxy; and
wherein $R^3$ is a group of the formula:—

-$A^1$-$Ar^2$-$A^2$-$Y^1$ in which $A^1$ is a bond between the α-carbon atom of the group CONHCH(CO$_2$H)— and $Ar^2$, or is a $C_{1-2}$ alkenyl group;
$Ar^2$ is phenylene, tetrazoldiyl, thiophenediyl, pyridinediyl or pyrimidinediyl which in the case of phenylene may optionally bear one or two substituent on the ring selected from halogeno, nitro, $C_{1-4}$alkyl, and $C_{1-4}$alkoxy;
$A^2$ is a $C_{1-3}$alkylene or $C_{2-3}$alkenylene group; and $Y^1$ is carboxy, tetrazol-5-yl, N—($C_{1-4}$alkylsulfonyl)carbamoyl,
N-(phenylsulfonyl)carbamoyl which may optionally bear one or two substituents on the phenyl ring selected from the group consisting of halogeno, nitro, $C_{1-4}$alkyl, and $C_{1-4}$alkoxy, tetrazol-5-ylthio, tetrazol-5-ylsulfinyl or tetrazol-5-ylsulfonyl; or
$Y^1$ is a group of the formula:—

—CON(R)CH($Y^2$)$Y^3$ in which R is hydrogen, $C_{1-4}$alkyl, $C_{3-4}$alkenyl or $C_{3-4}$alkynyl;
$Y^2$ is carboxy, tetrazol-5-yl, N—($C_{1-4}$alkylsulfonyl)carbamoyl, N-(phenylsulfonyl)carbamoyl which may optionally bear one or two substituents on
the phenyl ring selected from the group consisting of halogeno, nitro, $C_{1-4}$alkyl and $C_{1-4}$alkoxy, tetrazol-5-ylthio, tetrazol-5-ylsulfinyl or tetrazol-5-ylsulfonyl; and
$Y^3$ is the residue of a naturally occurring amino acid NH$_2$CH(CO$_2$H)$Y^3$; or
$Y^3$ is a group of the formula:—

-$A^4$-CO$_2$H in which $A^4$ is a $C_{2-6}$alkylene group other than ethylene;
wherein $R^3$ is a group of the formula:—

$A^5$-CON(R)CH($Y^4$)$Y^5$ in which $A^5$ is a $C_{1-6}$alkylene group and R is as defined above
$Y^4$ is carboxy, tetrazol-5-yl, N—($C_{1-4}$alkylsulfonyl)carbamoyl,
N-(phenylsulfonyl)carbamoyl which may optionally bear one or two substituents on the phenyl ring selected from the group consisting of halogeno, nitro, $C_{1-4}$alkyl and $C_{1-4}$alkoxy, tetrazol-5-ylthio, tetrazol-5-ylsulfinyl or tetrazol-5-ylsulfonyl; and
$Y^5$ is the residue of a naturally occurring amino acid NH$_2$CH(CO$_2$H)$Y^5$ provided that when R is hydrogen and $Y^4$ is carboxy it is not the residue of glutamic acid; or
$Y^5$ is a group of the formula:—

-$A^4$-CO$_2$H in which $A^4$ is as defined above; or
$Y^5$ is a group of the formula:—

-$A^6$-$Ar^3$-$A^7$-$Y^6$ in which $A^6$ is a bond between the α-carbon atom of the group -$A^5$-CON(R)CH($Y^4$) and $Ar^3$ or is a $C_{1-2}$alkylene group;
$Ar^3$ is phenylene, tetrazoldiyl, thiophenediyl, thiazolediyl, pyridinediyl or pyrimidinediyl which in the case of phenylene may optionally bear one or two substituents on the ring selected from halogeno, nitro, $C_{1-4}$alkyl and $C_{1-4}$alkoxy;
$A^7$ is a $C_{1-3}$alkylene or $C_{2-3}$alkenylene group; and
$Y^6$ is carboxy, tetrazol-5-yl, N—($C_{1-4}$alkylsulfonyl)carbamoyl,
N-(phenylsulfonyl)carbamoyl which may optionally bear one or two substituents on the phenyl ring selected from the group consisting of halogeno, nitro, $C_{1-4}$alkyl and $C_{1-4}$alkoxy, tetrazol-5-ylthio, tetrazol-5-ylsulfinyl or tetrazol-5-ylsulfonyl; or
wherein $R^3$ is a group of the formula:—

-$A^8$-X—$Ar^4$ in which $A^8$ is a $C_{1-4}$alkylene group;
X is sulfinyl, sulfonyl or methylene;
and $Ar^4$ is 1,2,3-triazol-4-yl, 1,2,4-triazol-3-yl or, except when X is methylene, tetrazol-5-yl;
the compound (VI) optionally being in the form of a pharmaceutically acceptable salt or ester.

Compounds of formula (I) and (VI) are of use as anti-cancer agents.

Particularly useful are compounds such as those disclosed in WO 03/020748, of general formula (VII)

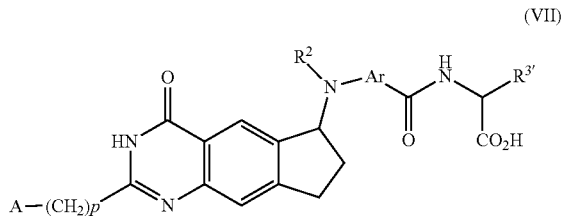

wherein A is $OR^{0'}$ or $NR^{0'}R^{1'}$ and $R^{0'}$ and $R^{1'}$ are each independently hydrogen, $C_{1-4}$alkyl, $C_{3-4}$alkenyl, $C_{3-4}$ alkynyl, hydroxy-$C_{2-4}$alkyl, halogeno-$C_{2-4}$alkyl or cyano-$C_{1-4}$alkyl, or $R^{0'}$ and $R^{1'}$ together with the intermediate N form a five- or six-membered heterocyclic ring;

p is an integer in the range 1 to 4;

Ar and $R^2$ are as defined above;

and wherein $R^{3'}$ may, for example, be a group of formula: -$A^5$-CON(R)CH($Y^4$)$Y^5$ in which $A^5$ is a $C_{1-6}$ alkylene group; R is hydrogen, $C_{1-4}$alkyl, $C_{3-4}$ alkenyl or $C_{3-4}$alkynyl; $Y^4$ is carboxy, tetrazol-5-yl, N—($C_{1-4}$alkylsulfonyl)carbamoyl, N-(phenylsulfonyl)carbamoyl which may optionally bear one or two substituents on the phenyl ring selected from halogeno, nitro, $C_{1-4}$alkyl and $C_{1-4}$alkoxy, tetrazol-5-ylthio, tetrazol-5-ylsulfinyl or tetrazol-5-ylsulfonyl; and $Y^5$ is the side chain of a naturally occurring amino acid or a group of the formula: -$A^4$-$CO_2H$ in which $A^4$ is as defined above.

In WO 03/020748, the synthesis of compounds of formula (II) is described, starting from 5-aminoindane. For example, compound 1 (N-{N-{4-[N-((6RS)-2-hydroxymethyl-4-oxo-3,4,7,8-tetrahydro-6H-cyclo-penta[g]quinazolin-6-yl)-N-(prop-2-ynyl)amino]benzoyl}-L-γ-glutamyl}-D-glutamic acid; 'BGC945') was prepared as shown in Scheme 1, below.

Scheme 1:

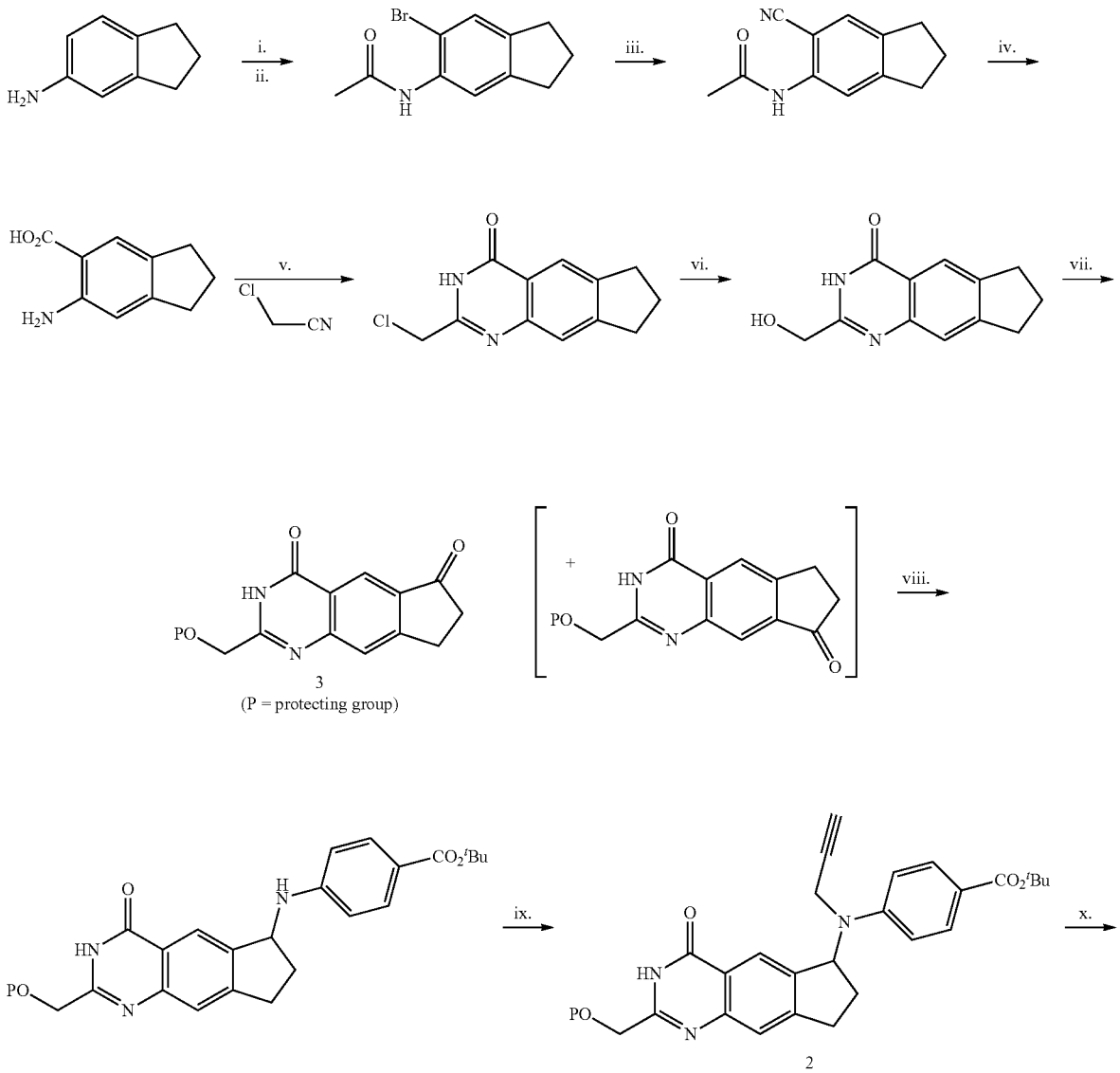

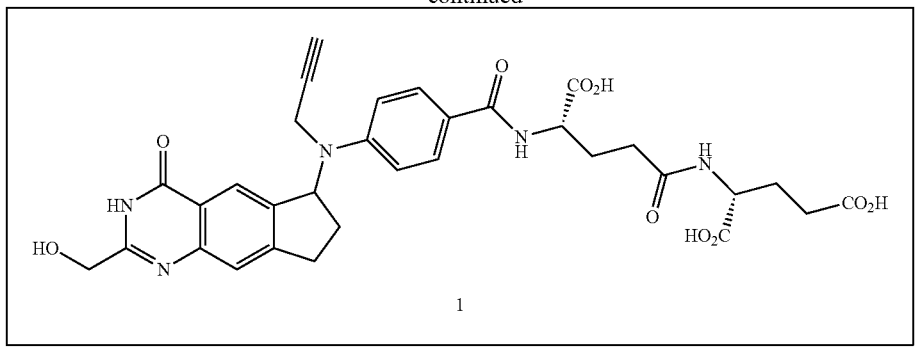

i. Ac₂O, AcOH, NaOAc;
ii. Br₂;
iii. CuCN, NMP;
iv. a) AcOH, HCl b) NaOH(aq);
v. NaOMe, ClCH₂CN;
vi. a) CsOAc b) NaOH(aq);
vii. a) e.g. Piv₂O, Et₃N, DMAP b) (Ph₃SiO)₂CrO₂ ᵗBuOOH;
viii. a) tert-butyl-4-aminobenzoate, decaborane;
ix. (propargyl)Co₂(CO)₆BF₄;
x. a) H⁺ b) tri-tert-butyl-L-γ-glutamyl-D-glutamate c) H⁺

An improved process for the synthesis of the key tricyclic intermediate, compound 2 is described in U.S. Pat. No. 7,250,511, and is shown in Scheme 2.

Scheme 2:

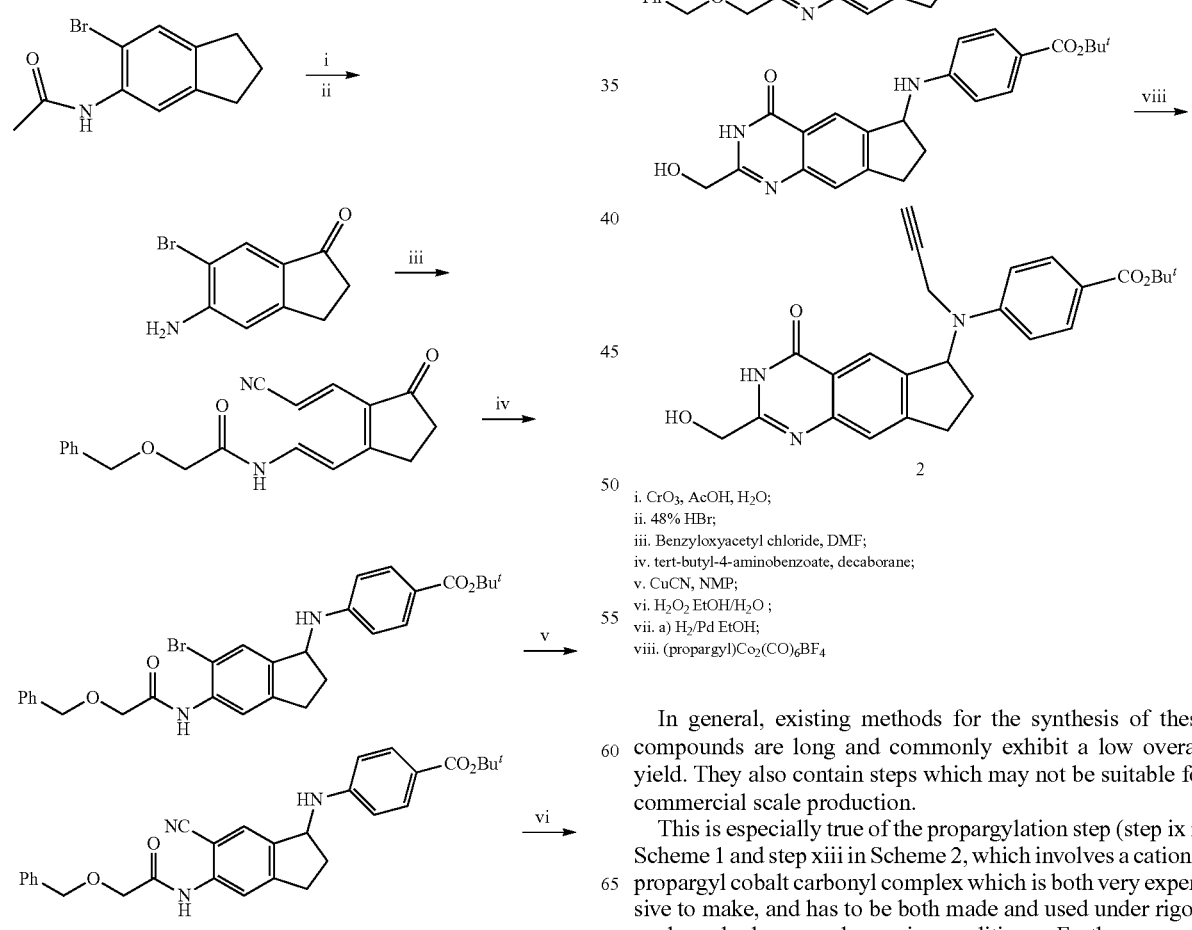

i. CrO₃, AcOH, H₂O;
ii. 48% HBr;
iii. Benzyloxyacetyl chloride, DMF;
iv. tert-butyl-4-aminobenzoate, decaborane;
v. CuCN, NMP;
vi. H₂O₂ EtOH/H₂O;
vii. a) H₂/Pd EtOH;
viii. (propargyl)Co₂(CO)₆BF₄

In general, existing methods for the synthesis of these compounds are long and commonly exhibit a low overall yield. They also contain steps which may not be suitable for commercial scale production.

This is especially true of the propargylation step (step ix in Scheme 1 and step xiii in Scheme 2, which involves a cationic propargyl cobalt carbonyl complex which is both very expensive to make, and has to be both made and used under rigorously anhydrous and anoxic conditions. Furthermore, it requires removal of the cobalt complex in an additional step. The reaction sequence becomes very problematic on scaling to even tens of grams. Thus it is unsuitable for commercial scale work. Additionally, although the disclosures cited above, and the disclosures in U.S. Pat. Nos. 7,297,701 and 7,528,141, all discuss the fact that compound 2 is produced as a racemate, making compound 1a 1:1 mixture of diastereoisomers, and that the 6S-isomer is the desired, more potent isomer, none of them reveal how to produce compound 2 in enantiomerically pure form without the use of additional steps of amide formation and enzymatic hydrolysis.

As discussed previously, the quantities and cost of the enzymes required, in addition to the fact that the resolution adds a minimum of three steps to the sequence (with the additional costs and losses of material that such inefficiency incurs) mean that these applications do not disclose a process which could be used on a production scale.

The present inventors have developed new processes for the synthesis of these compounds. These new synthetic processes will make the overall manufacturing route considerably shorter, and higher yielding, better capable of being run on a larger scale, and considerably less expensive than the current processes.

Furthermore, they reveal a highly feasible and fully scalable strategy for obtaining compound 2, and any desired analogues, in high enantiomeric purity, allowing compound 1 to be made efficiently in the desired 6S diastereoisomeric form in commercially useful amounts.

SUMMARY OF THE INVENTION

In one aspect, the present invention provides a process for producing a cyclopentaquinazoline from a 5-amino-6-haloindanone comprising the steps of:
(a) acylation of the 5-amino group;
(b) cyanide displacement of the 6-halo group;
(c) hydrolysis of the nitrile group produced in step (b); and
(d) cyclisation of a 5-amino-6-amidoindanone to form a cyclopentaquinazoline ring system.

In a further aspect, the invention provides a process for producing a cyclopentaquinazoline of general formula (VIII):

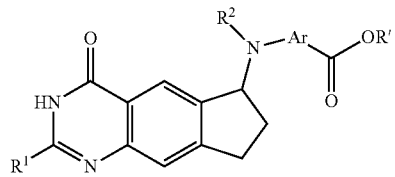

(VIII)

wherein $R^1$, $R^2$, Ar and R' are as defined herein, from a 5-amino-6-haloindanone of general formula:

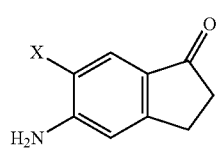

(IX)

wherein X is a halide.

In a further aspect the invention provides processes for the preparation of cyclopentaquinazoline compounds of general formulae (I), (VI) and (VIII)

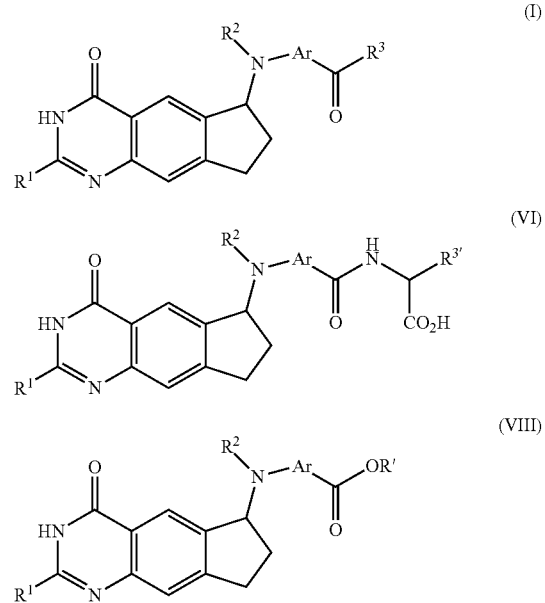

wherein $R^1$, $R^2$, R', Ar, $R^3$ and $R^{3'}$ are as defined herein.

Also provided are intermediate compounds, useful in the synthesis of cyclopentaquinazoline compounds, for example cyclopentaquinazoline compounds of general formulae (I), (VI) and (VIII), use of these intermediate compounds in the processes of the invention and methods for their synthesis.

Also provided is a method comprising chromatographic resolution of a compound of general formula (VIIIa) into its enantiomers:

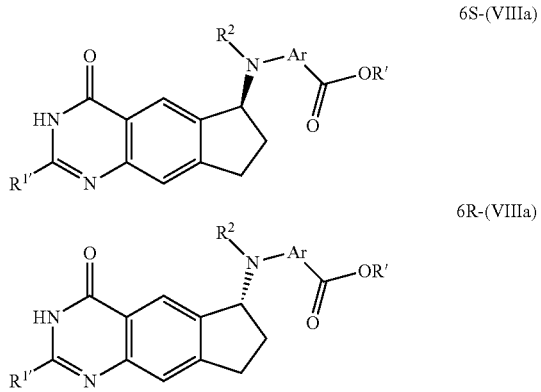

wherein $R^{1'}$, $R^2$, R', and Ar are as defined herein.

Also provided is an improved method for the synthesis of amines of general formula:

(XV)

wherein $R^2$, Ar and R' are as defined herein.

DETAILED DESCRIPTION OF THE INVENTION

Methods

The present invention provides novel methods for the preparation of a cyclopentaquinazoline compound from a 5-amino-6-haloindanone.

The methods typically comprise the steps of:
(a) acylation of the 5-amino group;
(b) cyanide displacement of the 6-halo group;
(c) hydrolysis of the nitrile group produced in step (b); and
(d) cyclisation of a 5-amino-6-amidoindanone to form a cyclopentaquinazoline ring system.

The steps may be performed in any suitable order.

In some embodiments, the steps are performed in the order: a), b), c), then d).

In other embodiments, the steps are performed in the order b), a), c) then d).

In other embodiments, the steps are performed in the order b), c), a) then d).

Other steps which may optionally be included in the methods of the invention include:
(e) reduction of the 1-keto group to produce an indan-1-ol
(f) coupling of an amine nucleophile to the indan-1-ol produced in step (e); and
(g) chromatographic resolution.

Other optional steps in the method may include protection, deprotection, and protecting group exchange steps, as well as any other necessary derivatisation and functional group manipulation steps.

5-Amino-6-Haloindanone Starting Materials

In the methods of the present invention, a cyclopentaquinazoline compound is prepared from a 5-amino-6-haloindanone.

In some embodiments, the 5-amino-6-haloindanone is a compound of formula (IX):

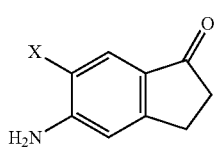

(IX)

wherein X is a halide.

In some embodiments, X is selected from —F, —Cl, —Br and —I.

In some embodiments, X is selected from —Cl and —Br.

In some embodiments, X is —Br.

(a) Acylation Step

Acylation of the 5-amino group comprises reaction of a 5-aminoindanone compound with an acylating agent. The product of the acylation step may be referred to as a 5-acylaminoindanone.

In some embodiments, acylation is carried out on the 5-amino-6-haloindanone starting material to produce a 5-acylamino-6-haloindanone.

In some embodiments, acylation is carried out on a compound of formula (IX), as defined above, to produce a compound of formula (X):

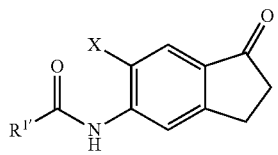

(X)

wherein X is as defined above and $R^{1'}$ is —$R^1$ or a derivative or protected form thereof.

In some embodiments, the acylation step comprises reacting the 5-amino-6-haloindanone with an acylating agent.

Acylation can be carried out with an acyl chloride, an anhydride, or other activated carboxylic acid derivative, such as a an acyl azide or pentafluorophenyl or 1-hydroxybenzotriazolyl ester, as are known in the art. Alternatively, acylation may be carried out by treatment of the amine with the appropriate carboxylic acid, in the presence of a coupling agent, such as a carbodiimide, eg DCC, EDC, a 2-halopyridinium salt, or activated aminophosphonium species such as BOP or PyBOP, as are known in the art. In certain preferred embodiments, the nitrogen of the amine group is acylated by reaction with a mixed anhydride produced, preferably in situ, by reaction of a carboxylic acid, with a chlorophosphate ester, most preferably diethylchlorophosphate.

In some embodiments the acylating agent comprises a carboxylic acid of formula $R^{1'}CO_2H$ and a coupling agent.

In some embodiments, the acylating agent is a mixed phosphoric anhydride generated in situ by reaction of a carboxylic acid of formula $R^{1'}CO_2H$ with a coupling agent.

In some embodiments, the coupling agent is a chlorophosphate ester.

In some embodiments, the coupling agent is diethylchlorophosphate.

In some embodiments, the coupling agent is used in the presence of a base.

In some embodiments, the base is triethylamine.

In some embodiments, the carboxylic acid is a compound of formula:

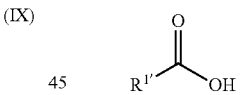

wherein $R^{1'}$ is selected from —$R^1$ or a derivative or protected form thereof, where $R^1$ is as previously defined.

In some embodiments, —$R^{1'}$ is selected from —$R^1$ where $R^1$ is as previously defined.

In some embodiments, $R^{1'}$ is —$R^1$ wherein R' is protected hydroxy$C_{1-4}$alkyl.

In some embodiments, the carboxylic acid is a compound of formula:

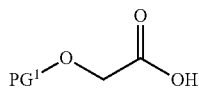

where $PG^1$ is a protecting group.

Suitable protecting groups for hydroxyl groups are known in the art and include, but are not limited to ether or ester protecting groups, for example: $C_{1-4}$ alkyl (e.g. t-butyl)ether; benzyl, benzhydryl (diphenylmethyl), or trityl (triphenylmethyl); trimethylsilyl or t-butyldimethylsilyl; or acetyl. Other protecting groups which may be suitable for use in the present invention can be found e.g. in "Protective Groups in Organic Synthesis" (T. Green and P. Wuts; 4th Edition; John Wiley and Sons, 2006).

In some embodiments, $PG^1$ is selected from benzyl (—CH₂Ph) and $C_{1-4}$ alkyl.

In some embodiments, $PG^1$ is $C_{1-4}$ alkyl. In some embodiments, $PG^1$ is t-butyl.

In some embodiments the carboxylic acid is benzyloxyacetic acid.

In some embodiments the carboxylic acid is t-butoxyacetic acid.

(b) Cyanation Step

Cyanation comprises conversion of the 6-halo group to a 6-nitrile. The product of this reaction may be referred to as a 6-cyanoindanone.

In some embodiments, cyanation is carried out on a 5-amino-6-haloindanone to produce a 5-amino-6-cyanoindanone.

In some embodiments, the cyanation is carried out on a 5-acylamino-6-haloindanone to produce a 5-acylamino-6-cyanoindanone.

In some embodiments cyanation is carried out on a compound of formula (X), as defined above, to produce a compound of general formula (XI):

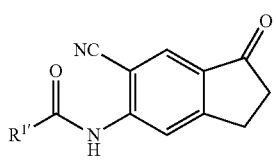

(XI)

wherein $R^{1'}$ is as defined above.

In some embodiments, cyanation comprises displacement of the 6-halo group with a cyanide nucleophile.

In some embodiments the cyanide nucleophile is selected from zinc cyanide, potassium cyanide, sodium cyanide, cuprous cyanide, or nickel cyanide, optionally in the presence of a catalyst.

In some embodiments the cyanide nucleophile comprises sodium or potassium cyanide in the presence of a catalyst.

In some embodiments the cyanide nucleophile comprises cuprous cyanide in the presence of a catalyst.

In some embodiments the cyanide nucleophile comprises zinc cyanide in the presence of a catalyst.

In some embodiments the cyanide nucleophile comprises nickel cyanide in the presence of a catalyst.

In some embodiments, the catalyst is a transition metal catalyst.

In some embodiments the transition metal is complexed with a triarylphosphine or with an arylated bisphosphine.

In some embodiments, the catalyst is a palladium catalyst.

In some embodiments, the catalyst is a nickel catalyst.

In some embodiments the catalyst is a crown ether

In some embodiments the catalyst is a quaternary ammonium salt

In some embodiments, the catalyst is selected from tetrakis (triphenylphosphine) palladium (Pd(PPh₃)₄), bis-(bis-[diphenylphosphino]ferrocene) palladium, tris(dibenzylideneacetone)dipalladium (Pd₂(dba)₃), tris (triphenylphosphine)nickel, and bis(triphenylphosphine) phenylnickel chloride In some embodiments, the catalyst is selected from tetrakis (triphenylphosphine) palladium (Pd(PPh₃)₄) and bis-(bis-[diphenylphosphino]ferrocene) palladium.

In some embodiments the catalyst is tetrakis(triphenylphosphine) palladium.

(c) Hydrolysis Step

Hydrolysis comprises conversion of the 6-nitrile produced in the cyanation step to an amido group (carboxamide). The product of this reaction may be referred to as a 6-amidoindanone.

In some embodiments, hydrolysis is carried out on a 5-amino-6-cyanoindanone to produce a 5-amino-6-amidoindanone.

In some embodiments, hydrolysis is carried out on a 5-acylamino-6-cyanoindanone to produce a 5-acylamino-6-amidoindanone.

In some embodiments, hydrolysis is carried out on a compound of formula (XI), as defined above, to produce a compound of general formula (XII):

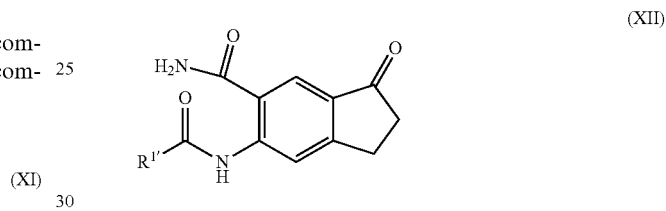

(XII)

wherein $R^{1'}$ is as defined herein.

Hydrolysis may be carried out by any method of nitrile hydrolysis known in the art.

In some embodiments, hydrolysis comprises treatment with acid.

In some embodiments, hydrolysis comprises treatment with formic acid.

In some embodiments, hydrolysis is carried out in the presence of magnesium sulfate.

In some embodiments, after treatment with acid, water is added.

In some embodiments, hydrolysis comprises treatment with hydrogen peroxide.

In some embodiments, hydrolysis comprises treatment with hydrogen peroxide in aqueous ethanol.

In some embodiments, hydrolysis comprises treatment with hydrogen peroxide and potassium carbonate in aqueous ethanol.

In some embodiments treatment with hydrogen peroxide is followed by treatment with an aqueous base.

In some embodiments the aqueous base is sodium hydroxide solution.

(d) Cyclisation Step

Cyclisation comprises conversion of a 5-acylamino-6-amidoindanone to a cyclopentaquinazoline. The product may be referred to as a 2-substituted cyclopenta[g]quinazoline-4,6-dione.

The intermediate a 5-acylamino-6-amidoindanone can be cyclised to the desired tricyclic cyclopenta[g]quinazoline-4, 6-dione, for example by treatment with a base.

In some embodiments, cyclisation comprises treatment of a compound of formula (XII) as defined above with a base, to produce a compound of formula (XIII):

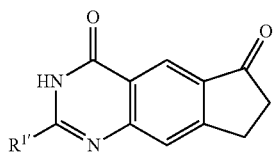

(XIII)

wherein R[1'] is as defined above.

In some embodiments, the base comprises an alkali metal alkoxide.

In some embodiments, the base comprises potassium t-butoxide.

In some embodiments, the base comprises sodium methoxide.

In some embodiments, the base is a solution of an alkali metal alkoxide in the corresponding alcohol.

In some embodiments, the base is a solution of sodium methoxide in methanol.

In some embodiments, the base is a solution of potassium t-butoxide in t-butanol.

In some embodiments the base comprises sodium or potassium hydroxide.

In some embodiments the base is a solution of sodium or potassium hydroxide in water, or in an alcohol, or in a mixed water-alcohol solvent system.

In some embodiments, the alcohol is selected from methanol or ethanol.

Depending on the exact chemistry used to generate the 5-(2-oxyacetamido)-indan-1-one-6-carboxamide, this cyclisation may be carried out automatically in situ during or immediately after the formation of the carboxamide, or the carboxamide may be isolated, and cyclised in a subsequent step.

In some embodiments, cyclisation occurs spontaneously upon formation of a 5-acylamino-6-amidoindanone in the preceding step.

In some embodiments, cyclisation occurs spontaneously upon formation of a 5-acylamino-6-amidoindanone in the hydrolysis step.

In some embodiments, cyclisation occurs spontaneously upon hydrolysis of a 5-acylamino-6-amidoindanone by treatment with hydrogen peroxide followed by treatment with an aqueous base.

In some embodiments, steps (c) and (d) are carried out consecutively.

In some embodiments, steps (c) and (d) are carried out consecutively by sequential additions of hydrogen peroxide, followed by concentrated aqueous base to the 5-acylamino-6-cyanoindan-1-one.

In some embodiments the base is sodium or potassium hydroxide.

In some embodiments, the base is at a concentration of about 6M.

In some embodiments, the hydrogen peroxide is at a concentration of 30% w/v (aq).

In some embodiments, the 5-acylamino-6-cyanoindan-1-one is as a mixture in an aqueous alcohol.

In some embodiments, the aqueous alcohol comprises 20% water in ethanol.

In some embodiments, addition is performed at 0-5° C.

In some embodiments, after addition, the mixture is allowed to warm to 25° C. and spontaneously exotherm, to form the cyclopentaquinazoline ring system.

In some embodiments, the crude cyclopentaquinazolinedione produced by the above methods is purified by crystallization, preferably from isopropanol/hexanes mixtures.

Further Steps

In some embodiments, the method of the invention further comprises conversion of the 2-substituted cyclopenta[g]quinazoline-4,6-dione product of steps (a) to (d) to compounds of general formula (I) to (VIII).

Conversion of the 2-substituted cyclopenta[g]quinazoline-4,6-dione to compounds of general formula (I) to (VIII) may be performed by methods known in the art, for example as disclosed in WO 03/020748 (see Scheme 1).

In some preferred embodiments, however, the 2-substituted cyclopenta[g]quinazoline-4,6-dione is subjected to further steps, comprising:

(e) reduction of the indanone keto group to produce an indanol (f) coupling of an amine nucleophile to the indanol produced in step (e).

In some embodiments, a further step comprising:
(g) chromatographic resolution;
is also performed.

Optionally, one or more further steps comprising:
(h) protecting group removal or protecting group exchange;
are also included.

(e) Reduction Step

The reduction step comprises reduction of the indanone keto group (the 6-keto group) of a cyclopenta[g]quinazoline-4,6-dione. The product may be referred to as an indanol.

In some embodiments, reduction is carried out on a cyclopenta[g]quinazoline-4,6-dione, to produce a 6-hydroxy-cyclopenta[g]quinazoline-4-one. In some embodiments, the cyclopenta[g]quinazoline-4,6-dione is the product of steps (a)-(d).

In some embodiments, reduction is carried out on a compound of formula (XIII) as defined above, to produce a compound of formula (XIV):

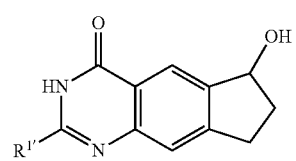

(XIV)

wherein R[1'] is as defined above.

In some embodiments, reduction comprises treatment of the cyclopenta[g]quinazoline-4,6-dione with a reducing agent.

Preferably, the reducing agent used is active enough to reduce the 6-keto group, but not reactive enough to cause reduction in the pyrimidone ring of the quinazoline.

In some embodiments, the reducing agent is a hydride based reducing agent.

In some embodiments, the reducing agent is selected from sodium borohydride, and formate salts in the presence of ruthenium diamine diphosphine catalysts for transfer hydrogenation.

In some embodiments, the reducing agent is sodium borohydride.

In some embodiments, the reducing agent is sodium borohydride in ethanol.

(f) Coupling Step

Coupling comprises conversion of the hydroxy group of the indanol into a leaving group, followed by reaction with an amine nucleophile.

In some embodiments, coupling is carried out on a 6-hydroxy-cyclopenta[g]quinazoline-4-one, to produce a 6-amino-cyclopenta[g]quinazoline-4-one.

In some embodiments, coupling comprises coupling a compound of formula (XIV) as defined above, with an amine of general formula (XV):

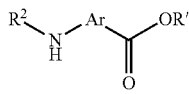

(XV)

to produce a compound of formula (VIIIa):

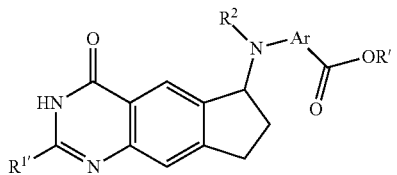

(VIIIa)

wherein $R^{1'}$, $R^2$, Ar and R' are as defined herein.

Converting the alcohol into a leaving group may be performed by any reaction which converts a hydroxy group (—OH) into a leaving group, i.e. a group which is more easily displaced by a nucleophile. Examples of leaving groups are well known in the art, and include mesylate, tosylate, nosylate, triflate, alkoxide, phenoxide, halide, phosphonate, phosphate, p-nitrobenzoate. Methods for converting hydroxy groups into leaving groups are commonly used in organic synthesis (See March's Advanced Organic Chemistry, 5th Edn. p 446 and references quoted therein. Smith, M. B.; March, J.) Wiley Interscience 2001)

In some embodiments conversion comprises a mesylation reaction.

In some embodiments, conversion comprises reaction of the alcohol with a mesylating agent selected from methanesulfonic anhydride ($Ms_2O$; $(MeSO_2)_2O$) or methanesulfonyl chloride (MsCl; $MeSO_2Cl$) to produce a mesylate group (—OMs; —$OSO_2Me$).

In some embodiments, conversion comprises reaction of the alcohol with methanesulfonic anhydride ($Ms_2O$; $(MeSO_2)_2O$).

In some embodiments, the mesylating agent is added portionwise.

In some embodiments conversion comprises conversion to a triflate (—OTf; —$OSO_2CF_3$).

In some embodiments conversion comprises reaction of the alcohol with trifluoromethanesulfonic anhydride ($Tf_2O$; $(F_3CSO_2)_2O$) or trifluoromethylsulfonyl chloride (TfCl; $F_3CSO_2Cl$).

In some embodiments, the conversion reaction is carried out at low temperature, for example at a temperature of 0° C. or below, preferably from −78° C. to 0° C. and most preferably from −40° C. to −20° C.

In some embodiments, conversion is carried out in the presence of a base.

In some embodiments, the base is an amine base.

In some embodiments, the base is a tertiary amine base.

In some embodiments, the base is a tertiary amine based selected from triethylamine and Hunig's base ($Et_2N^iPr$).

In some embodiments, the base is triethylamine.

In some embodiments, the base is used in excess.

Reaction with an amine nucleophile comprises treating the product of the conversion reaction with the amine nucleophile.

In some embodiments, conversion is carried out in situ i.e. the product of the conversion is not isolated but is reacted directly with the amine nucleophile.

In some embodiments, the amine, the indanol and a base are mixed together in a solvent and methanesulfonic anhydride is added to this mixture.

In some embodiments, the methanesulfonic anhydride is added in portions.

In some embodiments, the methanesulfonic anhydride is added in about 4-8 equal portions.

In some embodiments, a time of between about 10 and about 30 minutes is left between addition of each portion.

In some embodiments the solvent is a solvent of low ionic power.

In some embodiments, the solvent is selected from THF, dichloromethane, ethyl acetate, or isopropyl acetate.

In some embodiments, the base is a tertiary amine base.

In some embodiments, the base is a tertiary amine based selected from triethylamine and Hunig's base ($Et_2N^iPr$).

In some embodiments, the amine, the base and the methanesulfonic anhydride are each, independently, in 2-4-fold molar excess over the indanol.

In some embodiments, the amine nucleophile is used in an amount of about 2.5-3.5 molar equivalents compared to the indanol.

In some embodiments, the tertiary amine base is used in an amount of about 4-6 molar equivalents compared to the indanol.

In some embodiments, the methanesulfonic anhydride is used in an amount of about 2-3 molar equivalents compared to the indanol.

In some embodiments, the conversion reaction is carried out at a temperature of from 10-30° C.

The above alternative/preferred embodiments may be combined in any compatible combination, as will be understood by those skilled in the art. For example, in some embodiments, the indanol and about 2.5-3.5 equivalents of the amine nucleophile and 4-6 equivalents of a tertiary amine base, such as triethylamine or N-ethyldiisopropylamine, are mixed together to form a solution in a solvent of low ionic power, such as THF, dichloromethane, ethyl acetate or isopropyl acetate, and in the temperature range of 10-30° C., 2-3 equivalents of methanesulfonic anhydride, are added in 4-8 equal portions, with 10-30 minutes between each addition.

In some embodiments, the amine is O-t-butyl 4-(N-propargylamino)benzoate.

In some embodiments, the indanol is a 2-(oxymethyl)cyclopenta[g]quinazoline-4-on-6-ol.

In some embodiments, the indanol is 2-(t-butyldimethylsiloxymethyl)cyclopenta[g]quinazoline-4-on-6-ol.

In some embodiments, the indanol is 2-(t-butoxymethyl)cyclopenta[g]quinazoline-4-on-6-ol.

In some embodiments, the product of the coupling step is purified by crystallization from a suitable solvent.

Solvents for crystallisation include, but not limited to, methanol, isopropanol/hexanes mixtures and ethyl acetate.

For example, in some embodiments, a cyclopentaquinazoline of formula (VIIIa) is purified by crystallization from a solvent such as methanol, isopropanol/hexanes mixtures and ethyl acetate.

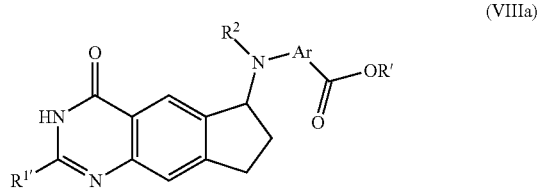

(g) Chromatographic Resolution

Resolution comprises separation of the enantiomers of the product of step (f) using chiral chromatography.

In some embodiments, resolution comprises separating a compound of formula (VIIIa) into its enantiomers:

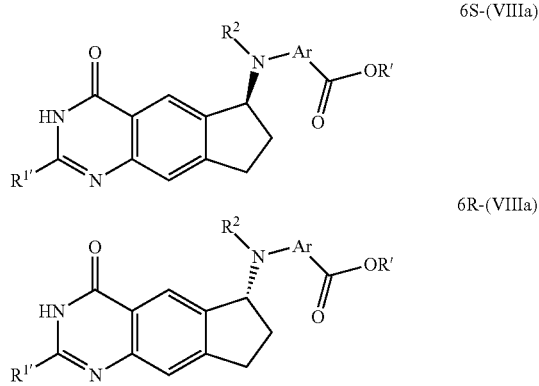

The product of the previous steps in this process is racemic. The inventors have found that it has very suitable properties for resolution by chiral chromatography on a chiral stationary phase. Various stationary phases (also referred to here as resins, regardless of whether they consist of a polymeric base, silica, polysaccharide, or other materials), solvents, and methods for chiral chromatography are known in the art.

Furthermore, the enantiomers may be obtained from the separation as amorphous solids, in high enantiomeric excesses, for example ≥99.8%, and with high chemical purities, for example in the 98-99% range. Addition of a crystallization step subsequent to the resolution, may provide crystalline material, with good handling characteristics and high purity, for example >99.8% by HPLC.

In some embodiments, chromatographic resolution comprises conventional single column chromatography using either low pressure (for example in a glass column apparatus), medium pressure (flash chromatography) or high pressure (High Performance Liquid Chromatography, HPLC).

In some embodiments, chromatographic resolution comprises supercritical fluid chromatography, using a solvent system containing an eluent in supercritical state such as carbon dioxide, a modifier such as methanol, ethanol or isopropyl alcohol in proportion in the range 0 to 60% by volume, and a chiral resin.

In some embodiments, chromatographic resolution uses a continuous multi column chromatography technique, such as simulated moving bed chromatography (SMB) or Varicol or any other variations known in the art and a chiral resin.

In some embodiments, the chiral resin is selected from resins including, but not limited to, Pirkle type resins including, but not limited to (S,S) or (R,R) Whelk-O1 resins (Regis Technologies, USA), or cellulose or amylose based resins such as ChiralCel OD, ChiralPak AD or Chiralpak IA (Daicel, Japan).

In some embodiments, chromatographic resolution comprises the use of (S,S)-Whelk-O1 resin, preferably packed in multiple columns for use in a simulated moving bed chromatographic apparatus.

In some embodiments, the solvent for elution comprises a solvent, or a mixture of solvents selected from linear or cyclic $C_6$-$C_8$ hydrocarbons, such as hexane or n-heptane, and a lower alcohol (methanol, ethanol, isopropanol, t-butanol); acetonitrile/lower alcohol (methanol, ethanol, isopropanol, t-butanol) mixtures; and dichloromethane/methyl t-butyl ether mixtures.

In some embodiments, chromatographic resolution comprises eluting with 40% dichloromethane/60% MTBE.

In some embodiments, chromatographic resolution comprises eluting with 40% methanol/60% acetonitrile.

In some embodiments, chromatographic resolution comprises simulated moving bed chromatography eluting with 40% methanol/60% acetonitrile on a Chiralpak AD® resin. In some embodiments, chromatographic resolution comprises simulated moving bed chromatography eluting with 40% dichloromethane, 60% methyl t-butyl ether on a (S,S)-Whelk-O1 resin.

In some embodiments, chromatographic resolution comprises simulated moving bed chromatography wherein (S,S)-Whelk-O1 resin is packed into a plurality of columns, portions of the racemate are loaded onto the columns in a solvent system, and eluted with the same solvent system.

In some embodiments, about 1 kg of (S,S)-Whelk-O1 resin is packed into eight 10 cm long columns and said columns are of internal diameter of about 50 mm.

In some embodiments the racemate is loaded into the apparatus in 0.5-1.0 kg lots dissolved in 40% dichloromethane, 60% methyl t-butyl ether at a concentration of about 16 g/L.

In some embodiments, loading is performed at a rate of about 35-45 mL/minute, and an operating pressure of about 25-35 bars.

In some embodiments, elution is performed with a 40% dichloromethane, 60% methyl t-butyl ether solvent mixture at a rate of about 100-250 mL/min.

In some embodiments, the desired amorphous enantiomer (6S-VIIIa), from the chiral chromatographic procedure is further purified and converted to a crystalline solid by crystallization from a suitable solvent system.

In some embodiments, the solvent system for the crystallisation is selected from isopropanol/hexanes and isopropanol/heptanes mixtures.

In some embodiments, the methods of the invention lead to an N-(cyclopentaquinazol-4-on-6-yl)-N-(propargyl)aminoarylcarboxylic acid (6S-VIIIa, R'=H, $R^1$=$CH_2OH$, $R^2$=propargyl, Ar=1,4-phenylene), which contains less than 0.4% of depropargylated material N-(cyclopentaquinazol-4-on-6-yl)-aminoarylcarboxylic acid (6S-VIIIa, R'=H, $R^1$=$CH_2OH$, $R^2$=H, Ar=1,4-phenylene.

$R^1$/$R^{1'}$ Chemistry and Protecting Group Manipulation

Further chemistry to manipulate the group at the 2-position of the cyclopentaquinazoline product (i.e. group $R^{1'}$), for example to deprotect or derivatise it to the group $R^1$ desired in the final product may be performed, if needed, at any suitable time during the synthesis, as will be evident to a person skilled in the art.

For example, in some embodiments, a protecting group forming part of the group $R^{1'}$ or $R^1$ may be exchanged for an alternative protecting group, which is more compatible with the reaction conditions of subsequent steps in the synthesis.

In some embodiments, protecting group exchange may involve deprotection of $R^{1'}$, followed by re-protection with an alternative protecting group.

For example, in some embodiments, $R^{1'}$ may be a group of formula —$CH_2$—O-$PG^1$, where $PG^1$ is a protecting group as previously defined. In these embodiments, protecting group exchange may be carried out, at any convenient point in the synthesis, to replace the original protecting group $PG^1$ with an alternative protecting group.

In some embodiments a benzyl protecting group is replaced with a tert-butyldimethylsilyl protecting group, using methods known in the art.

In some embodiments, a benzyl ether protecting group on $R^1$ is replaced with a tert-butyldimethylsilyl ether protecting group after the cyclisation step (d) and before the reduction step (e).

In some embodiments, protecting group exchange comprises debenzylation of $R^{1'}$ with aluminium trichloride.

In some embodiments, protecting group exchange comprises silylation by treatment with tert-butyldimethylsilyl chloride and imidazole.

In some embodiments, protecting group exchange comprises debenzylation of $R^{1'}$ with aluminium trichloride, followed by silylation with tert-butyldimethylsilyl chloride and imidazole.

Protecting Group Removal

Optionally, after resolution, one or more deprotection steps is carried out, to remove any remaining protecting groups and reveal the final product.

Conditions for the deprotection will depend on the nature of the protecting groups. Methods for the removal of common protecting groups are known in the art, see for example "Protective Groups in Organic Synthesis" (T. Green and P. Wuts; 4th Edition; John Wiley and Sons, 2006).

In some embodiments, deprotection comprises deprotection of a compound of formula (VIII) or (VIIIa) as defined above, to produce a final product of formula (VIII) wherein $R^1$ is selected from hydrogen, amino, $C_{1-4}$alkyl, $C_{1-4}$alkoxy, fluoro$C_{1-4}$alkyl, or hydroxy$C_{1-4}$alkyl; R' is hydrogen; and $R^2$ and Ar are as previously defined.

In some embodiments, removal of several protecting groups is effected in a single step.

In some embodiments, removal of protecting groups from $R^1/R^{1'}$ group and from the R' group in a compound of formula (VIII) or (VIIIa) is performed in a single step.

In some embodiments deprotection comprises treatment with acid.

In some embodiments the acid is selected from mineral acids and sulfonic acids.

In some embodiments, the acid is selected from strong acids with counterions of low nucleophilicity.

In some embodiments, the acid is selected from sulfuric acid, sulfonic acids, perchloric acid and tetrafluoroboric acid.

In some embodiments, the acid is methanesulfonic acid.

In some embodiments, the acid is methanesulfonic acid, of low water content, in acetonitrile solution.

In some embodiments, the acid is commercially available 70% aqueous methanesulfonic acid.

If methanesulfonic acid is used it can also serve as a solvent for the reaction. Commercially available 70% aqueous methanesulfonic acid is considerably cheaper than many other acids, and the presence of the water reduces any undesired exotherm.

In some embodiments, deprotection is performed at a temperature of about 5° C.

In some embodiments a protecting group on $R^1$ and the protecting group R' are removed in a single step from the N-(2-(protected)cyclopentaquinazol-4-on-6-yl)aminoarylcarboxylate ester 6S-(VIIIa), after resolution.

In some embodiments said protecting groups on $R^1$ and R' are removed by treatment of compound 6S-(VIIIa) with a strong non-nucleophilic acid, such as a sulfonic or sulfuric acid, in a suitable organic solvent.

In some embodiments, the reaction is performed at or below 25° C.

In some embodiments, the strong non-nucleophilic acid used is methanesulfonic acid. In this case, as mentioned above, the acid may also act as the solvent for the reaction. In some embodiments the methanesulfonic acid is at a concentration of 70 wt % in water. The initial temperature is preferably in the 20-25° C. range.

In some embodiments, the reaction is quenched by pouring onto cracked ice, and the resultant slurry is converted to a solution by basification (e.g. with sodium hydroxide) to pH 8-10, followed by reduction of the pH to 5 (e.g. with methanesulfonic acid) and then collection of the solid e.g. by suction filtration, after completion of a slow precipitation, and drying of the final product e.g. to 1-3% water by weight.

In some embodiments, globally deprotected N-(cyclopentaquinazol-4-on-6-yl)aminoarylcarboxylic acid (e.g. 6S-VIIIa, R'=H) is subjected to an isolation procedure.

In some embodiments, the isolation procedure comprises pouring the reaction mixture from the deprotection step into an excess of dilute sodium or potassium hydroxide solution.

In some embodiments, the dilute sodium or potassium hydroxide solution is cold e.g. at a temperature of 0-5° C.

In some embodiments, the dilute sodium or potassium hydroxide solution is provided with an external cooling bath, such that the temperature during the addition does not rise about 20° C.

In some embodiments, the dilute sodium or potassium hydroxide solution is preferably at a concentration of around 2M.

In some embodiment, the final pH of this mixture is equal to or greater than 10.

In some embodiments, the isolation procedure subsequently comprises addition of a dilute acid to precipitate the product.

In some embodiments, the dilute acid is added until the pH of the suspension is stabilized at about pH 5.

In some embodiments, the acid is dilute methanesulfonic acid.

In some embodiments, the acid is dilute aqueous methanesulfonic acid at a concentration of about 1M.

In some embodiments, addition of acid is followed by stirring, preferably until the precipitate is granular.

In some embodiments, during addition of the acid, the temperature is maintained in the 0-5° C. range.

In some embodiments the isolation procedure further comprises collecting the material by filtration or centrifugation, washing with water, and drying.

In some embodiments, resolved 2-protected (6S)-4,N-((2-(oxymethyl)-4-oxo-3,4,7,8-tetrahydro-3H-cyclopenta[g]quinazolin-6-yl)-N-(prop-2-ynyl)amino)benzoate esters are deprotected on the benzoic acid and hydroxymethyl moieties to give (6S)-4,N-((2-(hydroxymethyl)-4-oxo-3,4,7,8-tetrahydro-3H-cyclopenta[g]quinazolin-6-yl)-N-(prop-2-ynyl)amino)benzoic acid in good yield and purity.

Improved Synthesis of Amino-Benzoate Esters

Also provided is an improved method for the synthesis of amines of general formula:

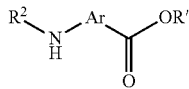  (XV)

wherein $R^2$, Ar and R' are as defined herein.

In particular an improved synthesis of O-t-butyl 4-(N-propargylamino)benzoates, i.e. compounds of formula (XV) where $R^2$ is propargyl and R' is t-butyl, is provided.

Amines of general formula (XV) may be prepared from 4-aminobenzoate esters of general formula $H_2N$—Ar—$CO_2R'$, where Ar and R' are as previously defined.

The method for the synthesis of amines of formula (XV) preferably comprises:
(i) trifluoroacetylation of a 4-aminobenzoate of general formula $H_2N$—Ar—$CO_2R'$, to produce a trifluoroacetamido-benzoate ester of general formula:

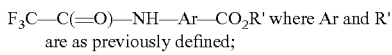

$F_3C$—C(=O)—NH—Ar—$CO_2R'$ where Ar and R' are as previously defined;

(ii) propargylation of said trifluoroacetamidobenzoate, to produce a (propargyl-trifluoroacetamido)benzoate of formula:

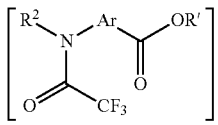

where $R^2$ is propargyl and Ar and R' are as previously defined; and
(iii) hydrolysis of the product of step (iii) in situ to give the desired amine of formula:

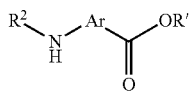  (XV)

where $R^2$ is propargyl and Ar and R' are as previously defined.

In some embodiments, step (i) comprises treatment of the 4-aminobenzoate with trifluoroacetic acid anhydride in pyridine.

In some embodiments, step (ii) comprises dissolution of said trifluoroacetamido-benzoate in a dipolar aprotic solvent, and treatment with a propargyl electrophile and an appropriate inorganic base In some embodiments, the dipolar aprotic solvent is selected from e.g. DMF, DMA and NMP.

In some embodiments, the propargyl electrophile is selected from propargyl chloride, propargyl bromide and propargyl mesylate.

In some embodiments, the inorganic base is selected from sodium carbonate, potassium carbonate, and caesium carbonate.

In some embodiments, step (ii) comprises dissolution of said trifluoroacetamido-benzoate in DMF, and treatment with propargyl bromide and potassium carbonate.

In some embodiments, in step (ii), the reaction is carried out at room temperature.

In some embodiments, in step (ii), the reaction is carried out at a temperature of about 35-45° C.

In some embodiments, in step (ii), the reaction is carried out for about 24 hours.

In some embodiments, in step (ii), 2 equivalents of propargyl bromide are used.

In some embodiments, in step (ii), the reaction is carried out with at least two equivalents of potassium carbonate.

In some embodiments, in step (ii), propargylation is monitored by an in process control.

In some embodiments, when an excess of potassium carbonate is employed, water is added to the reaction mixture after propargylation is shown to be at least 98% complete by an in process control.

In some embodiments, after water is added, stirring is continued for several hours at room temperature, until in process controls show that the trifluoroacetamide is completely hydrolyzed.

Compounds

The present invention provides methods and intermediates for the synthesis of cyclopentaquinazoline compounds. In some embodiments, the invention provides methods and intermediates for the synthesis of a 6-amino-cyclopenta[g]quinazoline compound.

In some embodiments, the invention provides methods for the synthesis of a cyclopentaquinazoline compound of general formula (VIII):

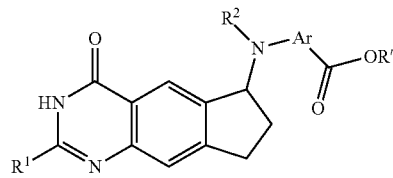  (VIII)

wherein $R^1$, $R^2$, Ar and a are as defined herein.

In some embodiments, an amino-cyclopentaquinazoline obtainable using the processes of the invention is an anti-cancer compound of general formula (I):

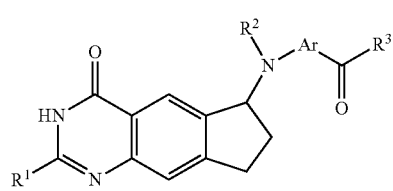  (I)

wherein $R^1$, $R^2$, Ar and $R^3$ are as defined herein.

In further embodiments, an amino-cyclopentaquinazoline obtainable using the processes of the invention is a compound of formula (VI):

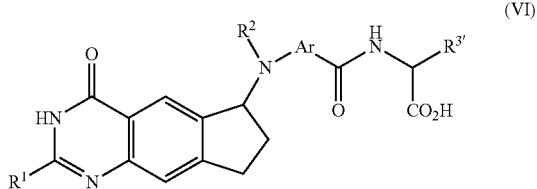

(VI)

wherein $R^1$, $R^2$, Ar and $R^{3'}$ are as defined herein.

Groups $R^1$, $R^2$, Ar, R', and $R^3$

In the compounds of formula (I), (II), (VI), (VII), and (VIII) the groups $R^1$, $R^2$, Ar, R', and $R^3$ are as defined herein.

The groups $R^1$, $R^2$, Ar, R', $R^3$, $R^{3'}$, $A^1$, $A^2_A{}^3$, $A^4$, $A^5$, $Y^1$, $Y^2$, $Y^3$, $Y^4$, $Y^5$, and R are defined herein as independent variables. As will be recognised by those skilled in the art, any compatible combination of these groups and substituents may be utilised in the compounds, methods and compositions of the present invention.

All compatible combinations of these and other defined variables are specifically embraced by the present invention, and are disclosed herein as if each and every combination were individually and explicitly recited.

$R^1$ $R^1$ is independently selected from hydrogen, amino, $C_{1-4}$alkyl, $C_{1-4}$alkoxy, fluoro$C_{1-4}$alkyl, hydroxy$C_{1-4}$alkyl, or protected hydroxy$C_{1-4}$alkyl.

In some embodiments, $R^1$ is independently selected from $C_{1-4}$alkyl, fluoro$C_{1-4}$alkyl, hydroxy$C_{1-4}$alkyl, or protected hydroxy$C_{1-4}$alkyl.

In some embodiments $R^1$ is selected from optionally protected hydroxy$C_{1-4}$alkyl.

In some embodiments $R^1$ is hydroxymethyl or protected hydroxymethyl.

$R^2$ $R^2$ is independently selected from hydrogen, $C_{1-4}$alkyl, $C_{3-4}$alkenyl, $C_{3-4}$alkynyl, hydroxy-$C_{2-4}$-alkyl, halo$C_{2-4}$alkyl or cyano$C_{1-4}$alkyl.

In some embodiments, $R^2$ is independently selected from $C_{1-4}$alkyl, $C_{3-4}$alkenyl, $C_{3-4}$alkynyl, hydroxy$C_{2-4}$alkyl, halo$C_{1-4}$alkyl and cyano$C_{1-4}$alkyl.

In some embodiments, $R^2$ is independently $C_{3-4}$alkenyl, $C_{3-4}$alkynyl, or cyano$C_{1-4}$alkyl.

In some embodiments. $R^2$ is independently $C_{3-4}$alkynyl.

In some embodiments, $R^2$ is independently propargyl.

Ar

Ar is independently selected from $C_{5-20}$ arylene, optionally substituted on the ring with one or two substituents selected from halogeno, hydroxy, amino, nitro, cyano, trifluoromethyl, $C_{1-4}$alkyl and $C_{1-4}$alkoxy.

In some embodiments, Ar is independently selected from phenylene, thiophenediyl, thiazolediyl, pyridinediyl or pyrimidinediyl, which may optionally bear one or two substituents selected from the group consisting of halogeno, hydroxy, amino, nitro, cyano, trifluoromethyl, $C_{1-4}$alkyl and $C_{1-4}$alkoxy.

In some embodiments, Ar is phenylene optionally substituted on the ring with one or two substituents selected from halogeno, nitro, $C_{1-4}$alkyl and $C_{1-4}$alkoxy.

In some embodiments, Ar is unsubstituted phenylene.

$R^3$ and $R^{3'}$ $R^3$ is a group of formula —NHCH($CO_2R''$)-$A^1$-$Y^1$ wherein $A^1$ is $C_{1-6}$alkylene, R" is hydrogen or a protecting group, and $Y^1$ is carboxy or a protected form thereof (i.e. —$CO_2R''$), tetrazol-5-yl, N—[$C_{1-4}$alkylsulfonyl]carbamoyl, N-(phenylsulfonyl)carbamoyl, tetrazol-5-ylthio, tetrazol-5-ylsulfinyl or tetrazol-5-ylsulfonyl, wherein said N-(phenylsulfonyl)carbamoyl group may optionally bear one or two substituents on the phenyl ring selected from halogeno, nitro, $C_{1-4}$alkyl and $C_{1-4}$alkoxy, or $Y^1$ is a group of the formula —CONH—CH($CO_2R''$)-$A^2$-$Y^2$ wherein the α-amino acid carbon atom has the D-configuration, $A^2$ is $C_{1-6}$alkylene and $Y^2$ is carboxy or a protected form thereof (i.e. —$CO_2R''$), or tetrazol-5-yl, wherein R" is hydrogen or a protecting group, or $R^3$ is a N-linked naturally-occurring amino acid selected from the group consisting of L-alanine, L-leucine, L-isoleucine, L-valine and L-phenylalanine or a suitable carboxy-protected form thereof, or $R^3$ is a group of the formula —NH-$A^3$-$Y^3$ wherein $A^3$ is $C_{1-3}$alkylene and $Y^3$ is phenyl which may optionally bear one, two or three substituents selected from the group consisting of halogeno, hydroxy, amino, nitro, cyano, trifluoromethyl, $C_{1-4}$alkyl and $C_{1-4}$alkoxy.

In some embodiments, $R^3$ is a group of formula —NHCH($CO_2R''$)-$A^1$-$Y^1$ wherein $A^1$ is $C_{1-6}$alkylene, R" is hydrogen or a protecting group, and $Y^1$ is carboxy or a protected form thereof (i.e. —$CO_2R''$), tetrazol-5-yl, N—[$C_{1-4}$alkylsulfonyl]carbamoyl, N-(phenylsulfonyl)carbamoyl, tetrazol-5-ylthio, tetrazol-5-ylsulfinyl or tetrazol-5-ylsulfonyl, wherein said N-(phenylsulfonyl)carbamoyl group may optionally bear one or two substituents on the phenyl ring selected from halogeno, nitro, $C_{1-4}$alkyl and $C_{1-4}$alkoxy, or $Y^1$ is a group of the formula —CONH—CH($CO_2R''$)-$A^2$-$Y^2$ wherein the α-amino acid carbon atom has the D-configuration, $A^2$ is $C_{1-6}$alkylene and $Y^2$ is carboxy or a protected form thereof (i.e. —$CO_2R''$), or tetrazol-5-yl, wherein R" is hydrogen or a protecting group.

$A^1$ is independently $C_{1-6}$alkylene.

In some embodiments, $A^1$ is independently selected from:
—$CH_2$—;
—$CH_2CH_2$—;
—$CH_2CH_2CH_2$—;
—$CH_2CH_2CH_2CH_2$—;
—$CH_2CH_2CH_2CH_2CH_2$—;
—$CH_2CH_2CH_2CH_2$—$CH_2CH_2$.

In some embodiments, $A^1$ is independently propylene (—$CH_2CH_2CH_2$—).

$Y^1$ is carboxy or a protected form thereof (i.e. —$CO_2R''$), tetrazol-5-yl, N—[$C_{1-4}$alkylsulfonyl]carbamoyl, N-(phenylsulfonyl)carbamoyl, tetrazol-5-ylthio, tetrazol-5-ylsulfinyl or tetrazol-5-ylsulfonyl, wherein said N-(phenylsulfonyl)carbamoyl group may optionally bear one or two substituents on the phenyl ring selected from halogeno, nitro, $C_{1-4}$alkyl and $C_{1-4}$alkoxy or $Y^1$ is a group of the formula —CONH—CH($CO_2R''$)-$A^2$-$Y^2$ wherein the α-amino acid carbon atom has the D-configuration, $A^2$ is $C_{1-6}$alkylene and $Y^2$ is carboxy or a protected form thereof (i.e. —$CO_2R''$), or tetrazol-5-yl, wherein R" is hydrogen or protecting group.

In some embodiments, $Y^1$ is independently carboxy or a protected form thereof (i.e. Y' is —$CO_2R''$, wherein R" is hydrogen or protecting group).

In some embodiments, $Y^1$ is independently carboxy (—$CO_2H$).

In some embodiments, $Y^1$ is a group of the formula —CONH—CH($CO_2R''$)-$A^2$-$Y^2$ wherein the α-amino acid carbon atom has the D-configuration, $A^2$ is $C_{1-6}$alkylene and $Y^2$ is carboxy or a protected form thereof (i.e. —$CO_2R''$) or tetrazol-5-yl, wherein R" is hydrogen or a protecting group.

$A^2$ is independently $C_{1-6}$alkylene.

In some embodiments, $A^2$ is independently selected from:
—$CH_2$—;
—$CH_2CH_2$—;
—$CH_2CH_2CH_2$—;

—CH$_2$CH$_2$CH$_2$CH$_2$—;
—CH$_2$CH$_2$CH$_2$CH$_2$CH$_2$—;
—CH$_2$CH$_2$CH$_2$CH$_2$—CH$_2$CH$_2$.

In some embodiments, A$^2$ is independently propylene (—CH$_2$CH$_2$CH$_2$—).

Y$^2$ is independently carboxy or a protected form thereof (i.e. —CO$_2$R″), or tetrazol-5-yl.

In some embodiments, Y$^2$ is independently carboxy or a protected form thereof (i.e. Y$^2$ is —CO$_2$R″, wherein R″ is hydrogen or a protecting group).

In some embodiments, Y$^2$ is independently carboxy (—CO$_2$H).

R$^{3'}$

In some embodiments, R$^3$ is independently a group of formula —NHCH(CO$_2$R″)R$^{3'}$.

R″ is hydrogen or a protecting group, as defined above.

R$^{3'}$ is a group of formula: -A$^5$-CON(R)CH(Y$^4$)Y$^5$ in which A$^5$ is a C$_{1-6}$ alkylene group; R is hydrogen, C$_{1-4}$alkyl, C$_{3-4}$ alkenyl or C$_{3-4}$alkynyl; Y$^4$ is carboxy or a protected form thereof (i.e. —CO$_2$R″), tetrazol-5-yl, N—(C$_{1-4}$alkylsulfonyl)carbamoyl, N-(phenylsulfonyl)carbamoyl which may optionally bear one or two substituents on the phenyl ring selected from halogeno, nitro, C$_{1-4}$alkyl and C$_{1-4}$alkoxy, tetrazol-5-ylthio, tetrazol-5-ylsulfinyl or tetrazol-5-ylsulfonyl; and Y$^5$ is the side chain of a naturally occurring amino acid or a group of the formula: -A$^4$-CO$_2$R″ in which A$^4$ is C$_{1-6}$ alkylene and R″ is hydrogen or a protecting group.

A$^5$ is independently C$_{1-6}$alkylene.

In some embodiments, A$^5$ is independently selected from:
—CH$_2$—;
—CH$_2$CH$_2$—;
—CH$_2$CH$_2$CH$_2$—;
—CH$_2$CH$_2$CH$_2$CH$_2$—;
—CH$_2$CH$_2$CH$_2$CH$_2$CH$_2$—;
—CH$_2$CH$_2$CH$_2$CH$_2$—CH$_2$CH$_2$.

In some embodiments, A$^5$ is independently propylene (—CH$_2$CH$_2$CH$_2$—).

R is hydrogen, C$_{1-4}$alkyl, C$_{3-4}$ alkenyl or C$_{3-4}$alkynyl.

In some embodiments, R is hydrogen or C$_{1-4}$ alkyl.

In some embodiments, R is hydrogen.

Y$^4$ is carboxy or a protected form thereof (i.e. —CO$_2$R″), tetrazol-5-yl, N—(C$_{1-4}$alkylsulfonyl)carbamoyl, N-(phenylsulfonyl)carbamoyl which may optionally bear one or two substituents on the phenyl ring selected from halogeno, nitro, C$_{1-4}$alkyl and C$_{1-4}$alkoxy, tetrazol-5-ylthio, tetrazol-5-ylsulfinyl or tetrazol-5-ylsulfonyl.

In some embodiments, Y$^4$ is carboxy or a protected form thereof (i.e. Y$^4$ is —CO$_2$R″, wherein R″ is hydrogen or a protecting group).

In some embodiments, Y$^4$ is carboxy (—CO$_2$H).

Y$^5$ is the side chain of a naturally occurring amino acid or a group of the formula: -A$^4$-CO$_2$R″ in which A$^4$ is C$_{1-6}$ alkylene and R″ is hydrogen or a protecting group.

In some embodiments, Y$^5$ is the side chain of a naturally occurring amino acid.

In some embodiments, Y$^5$ is a group of the formula: -A$^4$-CO$_2$R″ in which A$^4$ is C$_{1-6}$ alkylene and R″ is hydrogen or a protecting group.

A$^4$ is independently C$_{1-6}$alkylene.

In some embodiments, A$^4$ is independently selected from:
CH$_2$—;
—CH$_2$CH$_2$—;
—CH$_2$CH$_2$CH$_2$—;
—CH$_2$CH$_2$CH$_2$CH$_2$—;
—CH$_2$CH$_2$CH$_2$CH$_2$CH$_2$—;
—CH$_2$CH$_2$CH$_2$CH$_2$—CH$_2$CH$_2$.

In some embodiments, A$^4$ is independently ethylene (—CH$_2$CH$_2$—).

In some embodiments, R$^{3'}$ is a group of formula:

—CH$_2$CH$_2$C(=O)NHCH(CO$_2$H)CH$_2$CH$_2$CH$_2$CO$_2$H

R'

R' is hydrogen, or a protecting group.

In some embodiments, R' is hydrogen.

In some embodiments, R' is a protecting group.

In some embodiments, R' is a protecting group independently selected from C$_{1-4}$ alkyl, benzyl or allyl.

In some embodiments, R' is a C$_{1-4}$ alkyl protecting group.

R″

Each R″ is independently hydrogen or a protecting group.

In some embodiments, R″ is hydrogen.

In some embodiments, R″ is a protecting group.

In some embodiments, R″ is a protecting group independently selected from C$_{1-4}$ alkyl, benzyl, allyl, or a silyl protecting group.

In some embodiments, R″ is a silyl protecting group.

Various silyl protecting groups are known in the art (see, for example "Protective Groups in Organic Synthesis" 3$^{rd}$ Edn. TW. Greene and PGM Wuts Wiley New York, 1999).

In some embodiments, R″ is a silyl protecting group independently selected from trimethylsilyl (—SiMe$_3$), triethylsilyl (—SiEt$_3$), t-butyldimethylsilyl (–Si$^t$BuMe$_2$), phenyldimethylsilyl (—SiPhMe$_2$), t-butyldiphenylsilyl (—Si$^t$BuPh$_2$) or triisopropylsilyl (—Si$^i$Pr$_3$).

In some embodiments, R″ is a C$_{1-4}$ alkyl protecting group.

In some embodiments, R″ is selected from methyl, ethyl, i-propyl, n-propyl, t-butyl, i-butyl, s-butyl and n-butyl.

In some embodiments, R″ is t-butyl.

Certain Preferred Compounds

In some embodiments, a compound obtainable using the processes of the invention is a 6-amino-cyclopenta[g]quinazoline as disclosed in WO 94/11354, WO 95/30673, or WO 03/020748.

In some embodiments, the compound is a cyclopentaquinazoline compound of general formula (VIII) as defined above wherein R$^1$ is hydrogen, amino, C$_{1-4}$alkyl, C$_{1-4}$alkoxy, fluoroC$_{1-4}$alkyl, hydroxyC$_{1-4}$alkyl, or protected hydroxyC$_{1-4}$ alkyl; R$^2$ is C$_{3-4}$alkenyl C$_{3-4}$alkynyl, or cyanoC$_{1-4}$alkyl; Ar is phenylene optionally substituted on the ring with one or two substituents selected from halogeno, nitro, C$_{1-4}$alkyl and C$_{1-4}$alkoxy; and R' is hydrogen, or a protecting group selected from C$_{1-4}$ alkyl, benzyl or allyl.

In some embodiments, the compound is a cyclopentaquinazoline compounds of general formula (VIII) as defined above wherein R$^1$ is C$_{1-4}$alkyl, fluoroC$_{1-4}$alkyl, hydroxyC$_{1-4}$alkyl, or protected hydroxyC$_{1-4}$alkyl; R$^2$ is C$_{3-4}$alkenyl C$_{3-4}$alkynyl, or cyanoC$_{1-4}$alkyl; Ar is phenylene optionally substituted on the ring with one or two substituents selected from halogeno, nitro, C$_{1-4}$alkyl and C$_{1-4}$alkoxy; and R' is hydrogen, or a C$_{1-4}$ alkyl protecting group.

In some embodiments, the compound is a cyclopentaquinazoline compounds of general formula (VIII) as defined above wherein R$^1$ is hydroxymethyl or protected hydroxymethyl; R$^2$ is C$_3$alkynyl; Ar is unsubstituted phenylene; and R' is hydrogen, or a t-butyl protecting group.

In some embodiments, a compound obtainable by the methods of the invention is 4-(N-(2-(hydroxymethyl)-4-oxo-3,4,7,8-tetrahydro-3H-cyclo-penta[g]quinazolin-6-yl)-N-(prop-2-ynyl)amino]benzoic acid.

In some embodiments, a compound obtainable by the methods of the invention is N-{N-(4-[N-((6S)-2-hydroxymethyl-4-oxo-3,4,7,8-tetrahydro-6H-cyclo-penta[g]quinazolin-6-yl)-N-(prop-2-ynyl)amino]benzoyl}-L-γ-glutamyl}-D-glutamic acid. (ONX-0801).

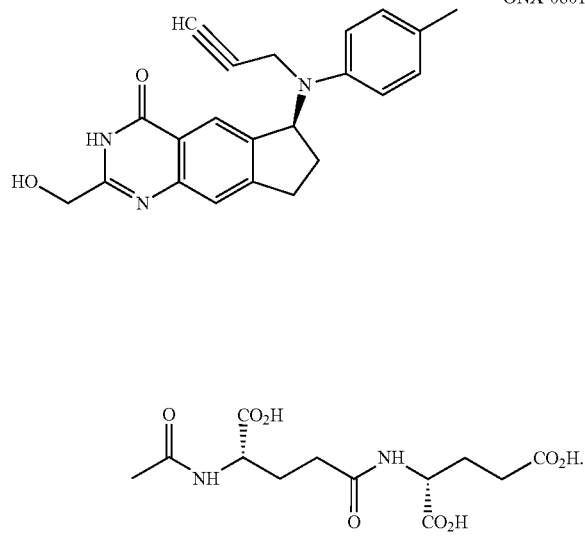

The present invention also provides certain compounds, useful as intermediates in the synthesis of cyclopentaquinazolines via the methods of the invention, and methods for their preparation.

These compounds may include the following:
5-(t-butoxyacetamido)-6-bromoindan-1-one;
5-(benzyloxyacetamido)-6-cyanoindan-1-one;
5-(t-butoxyacetamido)-6-cyanoindan-1-one;
6-aminocarbonyl-5-(benzyloxyacetamido)indan-1-one;
6-aminocarbonyl-5-(t-butoxyacetamido)indan-1-one;
2-(benzylyoxymethyl)-4,6-dioxo-3,4,7,8-tetrahydro-3H-cyclopenta[g]quinazoline;
2-(hydroxymethyl)-4,6-dioxo-3,4,7,8-tetrahydro-3H-cyclopenta[g]quinazoline;
2-(t-butoxymethyl)-4,6-dioxo-3,4,7,8-tetrahydro-3H-cyclopenta[g]quinazoline;
2-(t-butyldimethylsiloxymethyl)-4,6-dioxo-3,4,7,8-tetrahydro-3H-cyclopenta[g]quinazoline;
(R,S)-2-(t-butyldimethylsiloxymethyl)-6-hydroxy-4-oxo-3,4,7,8-tetrahydro-3H-cyclopenta[g]quinazoline;
(R)-2-(t-butyldimethylsiloxymethyl)-6-hydroxy-4-oxo-3,4,7,8-tetrahydro-3H-cyclopenta[g]quinazoline;
(S)-2-(t-butyldimethylsiloxymethyl)-6-hydroxy-4-oxo-3,4,7,8-tetrahydro-3H-cyclopenta[g]quinazoline;
(R,S)-2-(t-butoxymethyl)-6-hydroxy-4-oxo-3,4,7,8-tetrahydro-3H-cyclopenta[g]quinazoline;
(R)-2-(t-butoxymethyl)-6-hydroxy-4-oxo-3,4,7,8-tetrahydro-3H-cyclopenta[g]quinazoline;
(S)-2-(t-butoxymethyl)-6-hydroxy-4-oxo-3,4,7,8-tetrahydro-3H-cyclopenta[g]quinazoline; t-butyl (6RS)-4,N-((2-(t-butyldimethylsiloxymethyl)-4-oxo-3,4,7,8-tetrahydro-3H-cyclopenta[g]quinazolin-6-yl)-N-(prop-2-ynyl)amino)benzoate;
t-butyl (6S)-4,N-((2-(t-butyldimethylsiloxymethyl)-4-oxo-3,4,7,8-tetrahydro-3H-cyclopenta[g]quinazolin-6-yl)-N-(prop-2-ynyl)amino)benzoate;
t-butyl (6R)-4,N-((2-(t-butyldimethylsiloxymethyl)-4-oxo-3,4,7,8-tetrahydro-3H-cyclopenta[g]quinazolin-6-yl)-N-(prop-2-ynyl)amino)benzoate;
t-butyl (6RS)-4,N-((2-(t-butoxymethyl)-4-oxo-3,4,7,8-tetrahydro-3H-cyclopenta[g]quinazolin-6-yl)-N-(prop-2-ynyl)amino)benzoate;
t-butyl (6S)-4,N-((2-(t-butoxymethyl)-4-oxo-3,4,7,8-tetrahydro-3H-cyclopenta[g]quinazolin-6-yl)-N-(prop-2-ynyl)amino)benzoate;
t-butyl (6R)-4,N-((2-(t-butoxymethyl)-4-oxo-3,4,7,8-tetrahydro-3H-cyclopenta[g]quinazolin-6-yl)-N-(prop-2-ynyl)amino)benzoate.

The invention also relates to the following compounds, their use as intermediates in the synthesis of cyclopentaquinazolines via the methods of the invention, and improved methods for their synthesis:
5-(benzyloxyacetamido)-6-bromoindan-1-one;
(6S)-4,N-((2-(hydroxymethyl)-4-oxo-3,4,7,8-tetrahydro-3H-cyclopenta[g]quinazolin-6-yl)-N-(prop-2-ynyl)amino)benzoic acid;
(6R)-4,N-((2-(hydroxymethyl)-4-oxo-3,4,7,8-tetrahydro-3H-cyclopenta[g]quinazolin-6-yl)-N-(prop-2-ynyl)amino)benzoic acid;
(6RS)-4,N-((2-(hydroxymethyl)-4-oxo-3,4,7,8-tetrahydro-3H-cyclopenta[g]quinazolin-6-yl)-N-(prop-2-ynyl)amino)benzoic acid.

EXAMPLES AND DISCUSSION

The following examples are provided solely to illustrate and further explain the present invention, and are not intended to limit its scope. The discussion herein is focussed on specific embodiments of the invention, however it will be clear to those skilled in the art that the principles described will also be applicable to other compounds falling within the general definitions above.

In certain embodiments, two processes differing in the use of the 2-hydroxymethyl protecting group have been developed to make (6S)-4,N-((2-(hydroxymethyl)-4-oxo-3,4,7,8-tetrahydro-3H-cyclopenta[g]quinazolin-6-yl)-N-(prop-2-ynyl)amino)benzoic acid 4.

In the first route, shown in Scheme 3, the 2-hydroxymethyl group is initially protected as a benzyl ether. This proves to be robust, and allows the route to be carried through to the tricyclic dione 6 in good yields. However, conditions required to remove the benzyl group may not be compatible with cleanly retaining the propargyl group on the N6-amine, so an exchange of protecting groups is carried out at this stage.

Removal of the benzyl group proceeded best with $BCl_3$ on a small scale, which for reasons of cost was replaced with $AlCl_3$ on a larger scale. The crude alcohol produced by this benzyl cleavage reaction was treated with excess t-butyldimethylsilyl chloride, which converted it cleanly, after a chromatography, to the corresponding O-t-butyldimethylsilyl ether, 7, in ~51% overall yield for the two steps.

In a second preferred route, shown in Scheme 4, the 2-hydroxymethyl group is protected as a t-butyl ether at the beginning of the synthetic route, and this protecting group is compatible with all reaction conditions used subsequently, and is cleanly removed in the global deprotection in the final step. Some reactions are changed during the sequence from the original route, but overall, 2 steps are removed from the route and better yields and lower costs may be obtained.

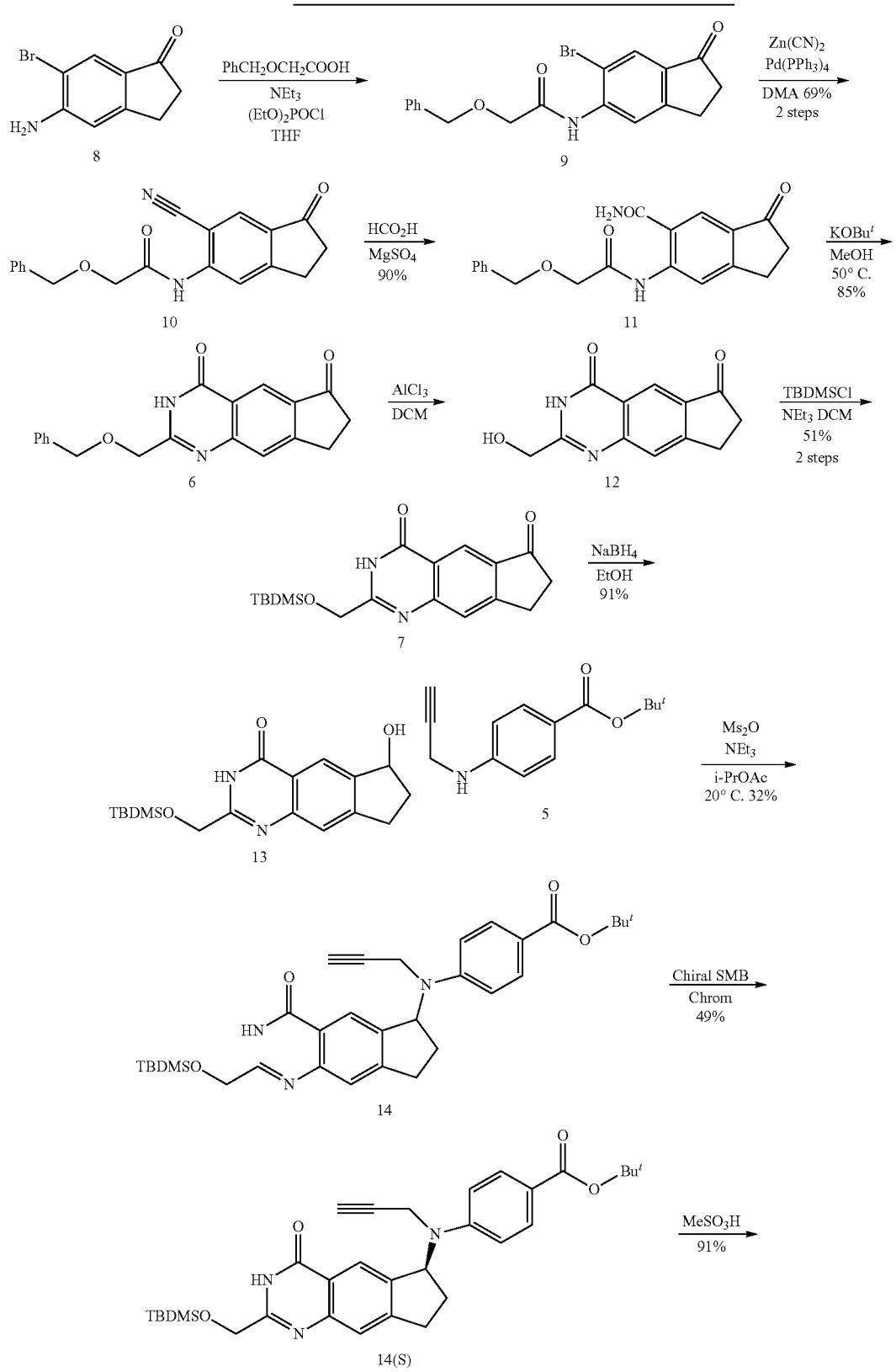
Scheme 3. Improved synthesis of 6S)-4,N-((2-(hydroxymethyl)-4-oxo-3,4,7,8-tetrahydro-3H-cyclopenta[g]quinazolin-6-yl)-N-(prop-2-ynyl)amino)benzoic acid 4, using benzyl, t-butyl, and t-butyldimethylsilyl protecting groups.

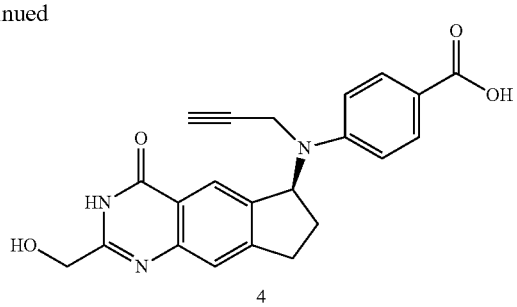

4

The use of benzyloxyacetyl chloride is described in U.S. Pat. No. 7,250,511 to convert 5-amino-6-bromoindan-1-one 8 into the corresponding amide 9. However, this process was found to be difficult to run on a large scale, and the yields were unsatisfactory, being only in the 60-65% range (uncorrected), and the purity was only around 80%.

Activation of benzyloxyacetic acid with diethyl chlorophosphate and triethylamine gave a mixed anhydride, which very efficiently acylates 5-amino-6-bromoindan-1-one 8 to the corresponding amide 9. Several standard coupling reagents, such as carbonyl diimidazole and isobutyl chloroformate were tried, but failed to produce acceptable quantities of amide 9. The discovery that the mixed phosphoric-carboxylic anhydride process works in good yield and high purity was unexpected.

The crude amide 9 was cyanated, with CuCN/NMP as described in WO 03/020748 for 5-acetamido-6-bromoindane. However, this reaction was not found to be at all feasible on a large scale, and palladium catalysed cyanation with zinc cyanide was examined instead. This was found to work satisfactorily with both tetrakis triphenylphosphine palladium, and bis-(bis-[diphenylphosphino]ferrocene) palladium, with somewhat better yields being obtained with the latter catalyst. Nitrite 10 produced that way was obtained in 68% overall yield from amine 8.

Hydrolysis of nitrile 10 to diamide 11 went very cleanly in formic acid containing magnesium sulfate at 40-50° C., followed by an aqueous work-up, to give 11 in 90% yield. In turn diamide 11 was cyclised by treatment with potassium t-butoxide in t-butanol or methanol at 50° C., to give tricyclic cyclopentaquinazolinedione 6 in 85% yield.

It was found that the benzyl group of the benzyl ether 6 could be removed cleanly with boron trichloride in dichloromethane, to give the free alcohol 12, but on a larger scale it was easier, and cheaper to use aluminium chloride in dichloromethane. Three molar equivalents of AlCl₃ were required to make the reaction go to completion, and although the reaction appeared clean by chromatography, the yield of 12 could not be determined, as the product could not be satisfactorily purified from precipitated aluminium salts. The crude alcohol 12 was silylated with t-butyldimethylsilyl chloride and triethylamine in dichloromethane, and the product was isolated after aqueous work-up, clean-up with activated charcoal and magnesol or filtrol, and a final heptane trituration to give quite clean silylated cyclopentaquinazolinedione 7 in 51% yield on the two steps.

Reduction of ketone 7 with sodium borohydride in ethanol at room temperature, followed by a solvent strip and aqueous-organic partitioning gave the pyrimidoindanol 13 in 90% yield.

The inventors also found that chiral reduction methods, many of which are known in the art, could be used to give the pyrimidoindanol in >90% e.e. For example reduction with sodium formate and tetrabutylammonium bromide in the presence of a chiral ruthenium catalyst provided the TBDMS protected indanol in 98% e.e.

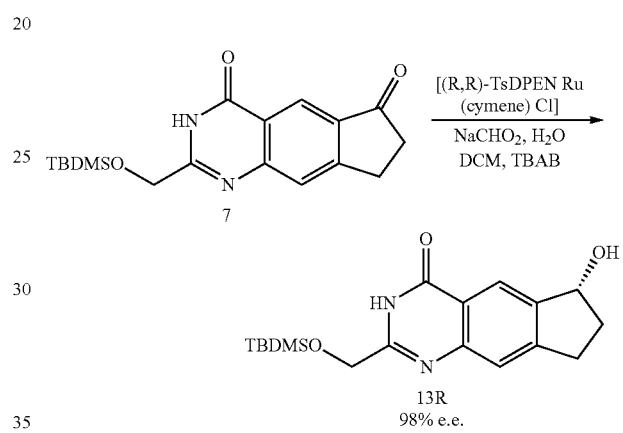

However, this enantiomeric purity was generally not maintained in the subsequent coupling step, and so a route involving later resolution was preferred.

The key coupling reaction between alcohol 13 and O-t-butyl 4-(N-propargylamino)benzoate 5 has several potential problems, as any electrophile made from 13 will be intrinsically unstable, with several potential unproductive decomposition mechanisms, and amine 5 is a highly deactivated nucleophile. Thus the two components are poorly matched, but by using a marked excess of amine 5, and by generating the mesylate in the presence of the nucleophile, in a not very ionizing solvent, a protocol was found which allows for 13 and 5 to be coupled together to form intermediate 14, which contains the entire molecular framework, in around 50% yield on a sub-kilo scale and 37% yield on a multi-kilo scale, based upon compound 13.

To carry this reaction out, a solution of alcohol 13, and 3.2 equivalents of amine 5, were dissolved in isopropyl acetate, containing 4.2 equivalents of triethylamine cooled to 10° C., and then 2.2 equivalents of methanesulfonic anhydride was added in several equal portions over a period of at least an hour. A considerable exotherm was noted after each addition. The reaction mixture was subjected to an aqueous work up and purified by column chromatography.

In general, it was found that the in situ generated 6-mesylates of 2-(oxymethyl)cyclopenta[g]quinazoline-4-on-6-ol react with simple O-alkyl esters of 4-(N-propargylamino) benzoate to form O-alkyl (6RS)-4,N-((2-(oxymethyl)-4-oxo-3,4,7,8-tetrahydro-3H-cyclopenta[g]quinazolin-6-yl)-N-(prop-2-ynyl)amino)benzoate derivatives in moderate to good yields based on the starting 2-(oxymethyl)cyclopenta[g]quinazoline-4-on-6-ol. The use of methanesulfonic anhydride as the sulfonating reagent, triethylamine or Hunig's base as the base, and THF, dichloromethane, ethyl acetate, or isopropyl acetate as the solvent, O-t-butyl 4-(N-propargylamino)benzoate as the amine, and 10-30° C. as the temperature range have been found to be advantageous.

The racemic compound 14 was resolved using a small simulated moving bed chromatography apparatus, with Chiralpak® AD® stationary phase, eluting with 40% MeOH in acetonitrile. This di-protected form of the desired acid 4 was obtained very efficiently with 97% recovery of the desired enantiomer, 14S in >99.9% EE. Treatment of 14S with methanesulfonic acid in acetonitrile, at 25° C., followed by an aqueous work-up and the use of sodium hydroxide to raise the pH to 5 gave the desired core acid 4 as a light brown solid in around 90% yield.

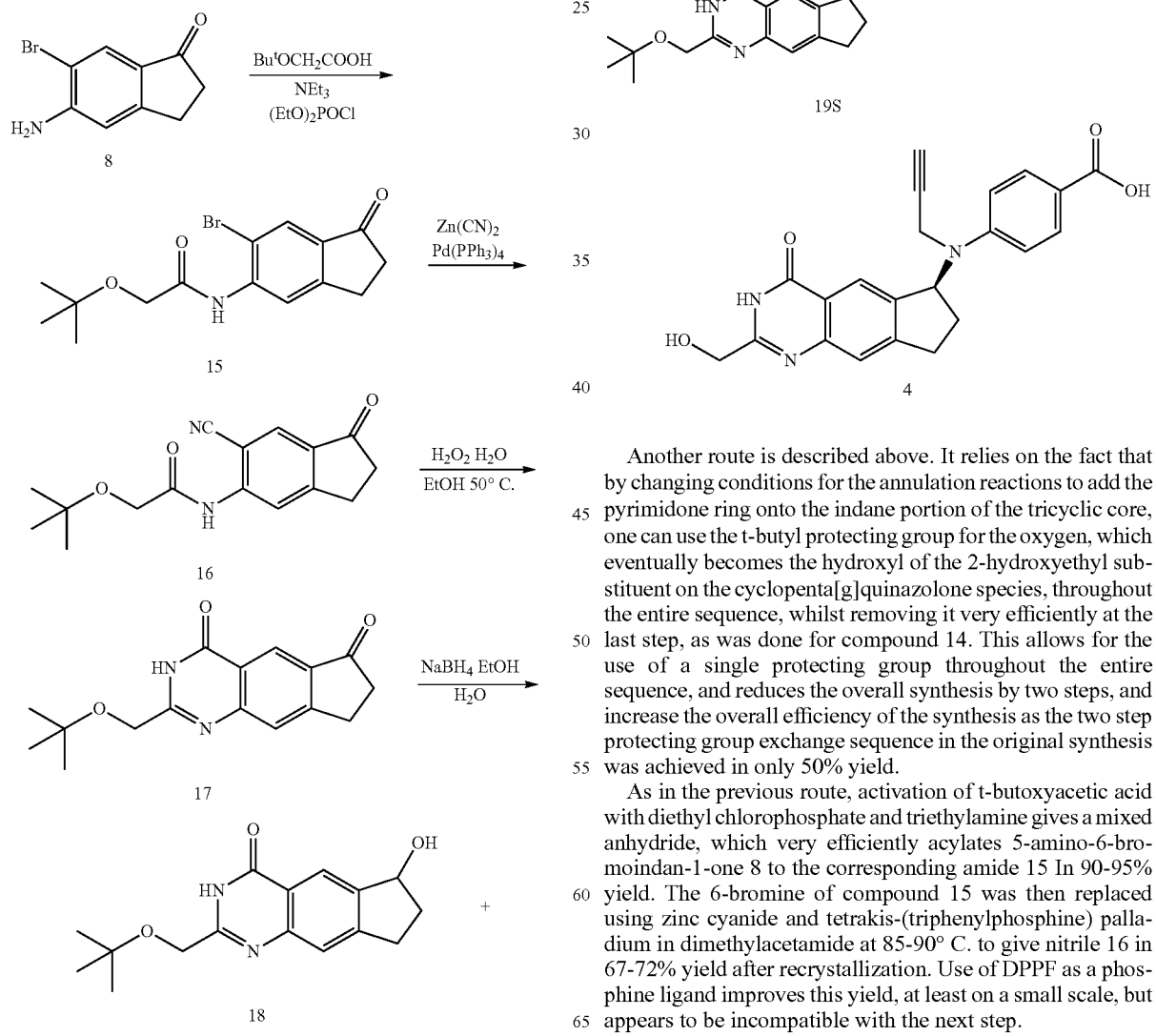

Another route is described above. It relies on the fact that by changing conditions for the annulation reactions to add the pyrimidone ring onto the indane portion of the tricyclic core, one can use the t-butyl protecting group for the oxygen, which eventually becomes the hydroxyl of the 2-hydroxyethyl substituent on the cyclopenta[g]quinazolone species, throughout the entire sequence, whilst removing it very efficiently at the last step, as was done for compound 14. This allows for the use of a single protecting group throughout the entire sequence, and reduces the overall synthesis by two steps, and increase the overall efficiency of the synthesis as the two step protecting group exchange sequence in the original synthesis was achieved in only 50% yield.

As in the previous route, activation of t-butoxyacetic acid with diethyl chlorophosphate and triethylamine gives a mixed anhydride, which very efficiently acylates 5-amino-6-bromoindan-1-one 8 to the corresponding amide 15 In 90-95% yield. The 6-bromine of compound 15 was then replaced using zinc cyanide and tetrakis-(triphenylphosphine) palladium in dimethylacetamide at 85-90° C. to give nitrile 16 in 67-72% yield after recrystallization. Use of DPPF as a phosphine ligand improves this yield, at least on a small scale, but appears to be incompatible with the next step.

Because of the acid-sensitive nature of the t-butyl protecting group, the formic acid hydrolysis of nitrile 16 is not used, and a one pot hydrolysis and cyclization using hydrogen peroxide in aqueous ethanol, followed by 6N sodium hydroxide solution at room temperature is used instead. This reaction requires careful handling, but after optimization produces the tricyclic cyclopentaquinazolinedione 17 in 71-83% yield on a multi-kilo scale. Residual traces of the DPPF catalyst from the previous step may cause rapid decomposition of the hydrogen peroxide, and are not compatible with this reaction sequence.

Reduction of ketone 17 with sodium borohydride in ethanol worked well, giving the corresponding pyrimidoindanol 18 in 90% yield. The inventors also found that chiral reduction methods, many of which are known in the art, could be used to give this pyrimidoindanol in >90% e.e. (e.g. as described above for the TBDMS-protected species). As this enantiomeric purity is generally not maintained in the subsequent coupling step, a route involving later chiral resolution is currently preferred.

Coupling of indanol 18 with O-t-butyl 4-(N-propargylamino)benzoate 5 was carried out under very similar conditions to those described above, giving the key fully protected core molecule 19 in 60-65% yield on medium scale, and 50% yield on a multi-kilo scale.

The crude product 19 from this reaction has somewhat different solubility characteristics from its silylated analogue 14, and it was found advantageous after stripping the organic extracting solvent to crystallize most of the crude oil from methanol, where about 58% of crude 19 was obtained on a nearly molar scale, and then chromatographing the residual oil to obtain another 17.7% of crude 19. Both of these materials were of rather low weight % purity. which can cause considerable problems in the next step, as the preferred technique of resolution, simulated moving bed chromatography, using a chiral packing material, works best when the separation being attempted is of a binary (enantiomeric) mixture, with other materials present tending to complicate the separation runs. Therefore, it was found advantageous to add a further crystallization step at this point, with the use of isopropanol/hexanes (or heptanes) particularly advantageous, with the purity being increased from <90 weight % purity to 98.2 weight percent purity, for an overall yield of 66%.

The somewhat different chromatographic and solubility properties of compound 19 from compound 14, led to differences in the resolution conditions to obtain the desired compound 19S. This resolution was carried out on a simulated moving bed apparatus using (S,S)-Whelk-O1 chiral stationary phase eluting with 40:60 dichloromethane:MTBE. This gave 19S in 99.8% enantiomeric excess with a recovery efficiency of 98.7% and a purity of >98% A. A final polishing recrystallization of 19S was carried out using isopropanol/heptanes, and gave a final yield of 83.9% with 99.8% EE and 99.93% A purity by hplc.

Initially, the same global deprotection conditions that were used for conversion of 14S into 4 were used to convert 19S into 4, However, on a large scale, the use of acetonitrile as the solvent for the methanesulfonic acid deprotection of 19S to the desired hydroxybenzoic acid 4 was found to be somewhat problematic, and eventually a simpler process was developed whereby solid 19S was added directly to a commercially available 70% aqueous methanesulfonic acid solution, cooled initially to 0° C.

It has been found that under strongly acidic conditions, the 6-amino group is protonated, and that this species is susceptible to nucleophilic attack at the 1-propargyl position, leading to N-depropargylation. Therefore, more preferred conditions for this deprotection involve the use of strong acids with counterions of low nucleophilicity, such as sulfuric acid, sulfonic acids, perchloric acid and tetrafluoroboric acid. Methanesulfonic acid has been found to be especially preferable, as it can also serve as a solvent for this reaction. Commercially available 70% aqueous methanesulfonic acid has been found to be the most preferred solvent for this reaction.

The use of this solution is economically desirable as it is rather cheaper than anhydrous methanesulfonic acid, and it was found that the presence of the water prevents a somewhat problematic exotherm, making the reaction easier to control on a large scale. The work-up of this reaction was also modified. It was found that pouring the reaction solution onto crushed ice, and then basifying the resultant highly acidic solution with concentrated sodium hydroxide solution all the way to pH 8, led to another solution, which produced a considerably better quality of precipitate when the pH was subsequently lowered to 5, by addition of methanesulfonic acid, than when less sodium hydroxide was used to simply raise the reaction pH directly to 5. Alternatively, when the reaction is complete by HPLC, the methanesulfonic acid mixture may be transferred slowly to a solution of cold (5° C.) solution of 2N NaOH, equipped with an external cooling bath so that the temperature does not rise above 20° C. During the quench, a solid forms which then redissolves in the basic solution. By the time all of the deprotection solution has been added to the base, no solid is present. The solid may then be reprecipitated with the addition of a small amount of 1M aqueous methanesulfonic acid.

The acid 4 produced by this process could be dried to a water content of 0.7-3.0 wt % and used directly in the final synthesis of compound 1.

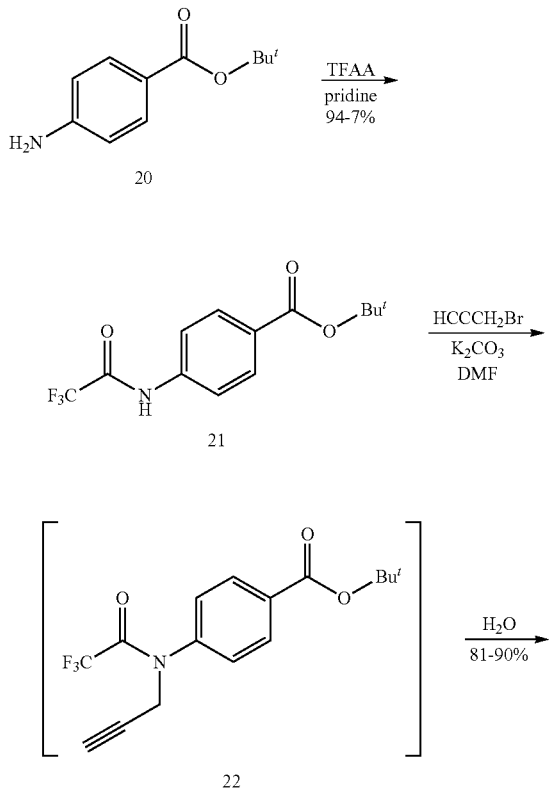

Scheme 5. An Efficient Synthesis of O-t-Butyl 4-(N-propargylamino)benzoate 5

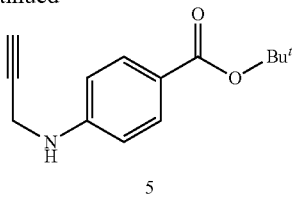

5

A further component of this invention is a simple three-step, two-pot, preparation of the key amine intermediate O-t-butyl 4-(N-propargylamino)benzoate 5, illustrated in Scheme 5 above. As amine 5 has to be used in a threefold molar excess during the coupling reaction, and then half of the coupled product has to be discarded because it is the wrong enantiomer, the cost of amine 5 is seen disproportionately in the final cost of goods, and the cheapest synthesis possible of 5 is required. A very efficient and short sequence for making amine 5 from O-t-butyl 4-aminobenzoate 20 is described in this application. Treatment of amine 20 with trifluoroacetic acid anhydride in pyridine leads quantitatively to trifluoroacetylation of the 4-amine to form O-t-butyl 4-(trifluoroacetamido)benzoate 21, which can be isolated in 94-97% yield, and greater than 99% purity on a multi-kilo scale. Dissolution of amide 21 in DMF, and treatment with 2 equivalents of propargyl bromide, and three equivalents of potassium carbonate for 24 hours at room temperature leads to near quantitative formation of O-t-butyl 4-(N-propargyltrifluoroacetamido)benzoate 22, which is not isolated, but simply hydrolyzed by addition of water, which with the excess potassium carbonate already in solution gives a solution with a pH around 10. The desired product, amine 5, precipitates in 81-90% yields and a purity of 97-98%, with the only appreciable impurity being unreacted starting material 20. As compound 20 can in theory lead to a difficult to remove despropargyl impurity in the coupling reaction, recrystallization of 5 to greater purity was initially used, but led to about a 50% loss in overall yield. After subsequent experiments showed that unexpectedly, compound 20 does not couple with compounds 13 and 18 under the standard coupling conditions described above, the process was switched to using unrecrystallized amine 5, which means that this process generates amine 5, suitable for use in the synthesis of compound 4 by the process described in this application, in two reactors and 77-87% overall yield.

Experimental Section 5-(Benzyloxyacetamido)-6-bromoindan-1-one 9

A 15 mL, 1 neck flask was equipped with a magnetic stirrer, a reflux condenser and a $N_2$ inlet. The flask was charged with benzyloxyacetic acid (166 mg, 0.001 mol) and dry dichloromethane (4 mL). To the solution was added diethyl chlorophosphate (0.36 mL, 0.0025 mol) followed by the dropwise addition of triethylamine (0.35 mL, 0.0025 mol). The reaction mixture was allowed to stir at room temperature for one hour and then 5-amino-6-bromo-1-indanone (226 mg, 0.001 mol), (weight uncorrected for a purity of about 90%) and triethylamine (0.35 mL, 0.0025 mol) was added. The reaction was refluxed for 24 hours and an aliquot was removed and analyzed by HPLC. The reaction was approximately 80% complete. The solvent was removed on the rotary evaporator affording a brown viscous residue. To the residue was added 4 mL of a 20% methanol/water mixture. A free flowing solid formed which was filtered off, washed with 4 mL of cold (0° C.) methanol and dried without heating in the vacuum oven. 220 mg (59%) of the desired benzyloxyacetamide 9 was obtained as a tan powder after drying. TLC Analysis: $R_f$ 0.68 (50% EtOAc/hexanes). HPLC 10:90 to 90:10 $CH_3CN:H_2O$ over 15 min. Hold at 90:10 for 2 min, 0.025% TFA Buffer, 1.5 mL/min, UV at 220 nm, Phenomenex Jupiter C18 column 4.6 mm×250 mm at 29° C.: (11.17 min, 94.3 A %)$^1$H NMR ($CDCl_3$, 400 MHz): 2.65-2.75 (m, 2H), 3.05-3.15 (m, 2H), 4.17 (s, 2H), 4.72 (s, 2H), 7.30-7.50 (m, 5H), 7.95 (s, 1H), 8.65 (s, 1H), 9.39 (br, 1H).

5-(Benzyloxyacetamido)-6-cyanoindan-1-one 10

A 12 L, 4 neck flask was equipped with an overhead stirrer, an N2 inlet, a type-J Teflon® covered thermocouple, solid addition funnel, and a reflux condenser. The flask was charged with 2-benzyloxy-N-(6-bromo-I-oxoindan-5-yl)acetamide (2000 g, 5.35 mol), as is weight uncorrected for a purity of about 85-90%) and DMAC (3320 ml). Nitrogen was bubbled through the resulting dark viscous solution for 40 minutes. To this stirring solution was added $Pd_2(dba)_3$ (52.4 g, 57.0 mmol) followed by DPPF (58.4 g, 105 mmol). The resulting slurry was then heated to 85° C. and was treated with solid $Zn(CN)_2$ (372 g, 3.18 mol) portion-wise over a period of 2 hours. The reaction was stirred at 85° C. for 3 hours. At that time the reaction was judged to be complete (by LC and TLC) and was then allowed to cool to 20° C. and stir overnight at that temperature under an atmosphere of $N_2$. The following morning the reaction mixture was split into two equal portions. Each half was diluted with 12 L of water resulting in the formation of a yellow precipitate. The yellow solid from each portion was collected by vacuum filtration rinsing with water (12 L) followed by IPA (500 ml). The combined solids were allowed to air dry in a fume hood to afford 1701 g (1225 g, 85% yield-corrected for a product purity of 72% by weight and a starting material purity of 85%) of a yellow powder. This material was used directly in the next step without purification. TLC Analysis: Rf=0.28 (50% EtOAC/hexanes). HPLC 10:90 to 90:10 $CH_3CN:H_2O$ over 15 min. Hold at 90:10 for 2 min, 0.025% TFA Buffer, 1.5 mL/min, UV at 220 nm, Phenomenex Jupiter C18 column 4.6 mm×250 mm at 29° C.: (11.68 min, 93 A %) $^1$H NMR ($CDCl_3$, 300 MHz): 2.70-2.76 (m, 2H), 3.16-3.23 (m, 2H), 4.16 (s, 2H), 4.74 (s, 2H), 7.32-7.45 (m, 5H), 7.98 (s, 1H), 8.69 (s, 1H), 9.30 (br, 1H).

6-Aminocarbonyl-5-(benzyloxyacetamido)indan-1-one 11

A 22 L, 3 neck flask, equipped with an overhead stirrer, electric heating mantle, condenser, an $N_2$ inlet, and a type-J Teflon® covered thermocouple, was charged with nitrile 10 (797 g, 2.49 moles—corrected for a purity of 75% by weight), formic acid (6400 ml) and magnesium sulfate (510 g). The resulting brown viscous mixture was heated to 40° C. with stirring and was allowed to stir at that temperature for 4 hours. At that time the reaction was judged to be complete by TLC and LC analysis. The reaction mixture was allowed to cool to 20° C. and stir at that temperature overnight. The following morning the reaction mixture was poured into 24 liters of water. The resulting yellow solid was collected by vacuum filtration rinsing with water (2×1500 ml) followed by isopropanol displacement wash (1×1500 ml). The crude product was allowed to air dry to a constant weight to afford 1030 g (886 g corrected for purity of 86% by weight-103%). The water content was 1.02% by Karl Fischer titration. The material was used directly in the next step without further purification. Rf=0.37 (65% EtOAc/hexanes) HPLC 10:90 to 90:10

CH$_3$CN:H$_2$O over 15 min. Hold at 90:10 for 2 min, 0.025% TFA Buffer, 1.5 mL/min, UV at 220 nm, Phenomenex Jupiter C18 column 4.6 mm×250 mm at 29° C.: (st. material 11.6 min, amide 9.26 min, 87 A %) $^1$H NMR (DMSO, 300 MHz): 2.61-2.65 (m, 2H), 3.09-3.13 (m, 2H), 4.13 (s, 2H), 4.64 (s, 2H), 7.29-7.49 (m, 5H), 7.84 (br, 1H), 8.12 (s, 1H), 8.49 (br, 1H), 8.74 (s, 1H), 12.57 (br, 1H).

2-(Benzylyoxymethyl)-4,6-dioxo-3,4,7,8-tetrahydro-3H-cyclopenta[g]quinazoline 6

A 12 L, 3 neck flask was equipped with a Caframo type RZR50 overhead mechanical stirrer connected to a ³⁄₁₆" thick banana shaped solid Teflon® stir paddle with a 19 mm diameter glass stir shaft, pressure equalizing addition funnel, a N$_2$ inlet, and a type-J Teflon® covered thermocouple was charged with carboxamide 11 (469 g, 1.39 mol corrected for purity of 86% by weight) and t-BuOH (5450 ml). The resulting slurry was heated to 50° C. and was treated with a 1M solution of KOt-Bu in t-BuOH (1600 ml, 1.60 mol) over a period of 25 minutes. The reaction mixture became extremely viscous as the addition progressed. After the addition was complete the reaction was allowed to stir at 50° C. for an additional 90 minutes. At that time the reaction was judged to be complete by TLC and LC analysis. The reaction was then allowed to cool to 30° C. and was diluted with water (4000 ml). The pH of the resulting dark solution was adjusted to 7 by the addition of 630 ml of 2.5 M hydrochloric acid. The reaction mixture was then transferred to a Buchi rotovap and the t-BuOH was distilled off under reduced pressure (60 mbar) with heating (45° C. water bath). The resulting aqueous mixture was returned to the original reaction vessel and cooled to 10° C. The pH of that mixture was lowered to 4 by the addition of 2.5M hydrochloric acid. The resulting yellow solid was collected by vacuum filtration rinsing with water (2×1000 ml). The filter cake was allowed to dry in the funnel overnight and was then transferred to a shallow aluminum foil lined tray and was allowed to air dry in a fume hood for two or three days to afford 518 grams of a yellow powder. This material was 75% pure by weight for a corrected yield of 388 gms (87%), and contained 5% water by Karl Fischer titration. Rf=0.25 (65% EtOAC/hexanes). The material was dried further at 75° C. for 24 h in an oven with a nitrogen sweep until the water content was 0.5% by KF titration. HPLC 10:90 to 90:10 CH$_3$CN:H$_2$O for 15 min. Hold at 90:10 for 2 min, 0.025% TFA Buffer, 1.5 mL/min, UV at 220 nm, Phenomenex Jupiter C18 column 4.6 mm×250 mm at 29° C.: (it 8.83 min, 98 A %)$^1$H NMR (CDCl$_3$, 300 MHz): 2.74-2.81 (m, 2H), 3.24-3.32 (m, 2H), 4.56 (s, 2H), 4.72 (s, 2H), 7.32-7.45 (m, 5H), 7.65 (s, 1H), 8.68 (s, 1H), 9.80 (br, 1H).

2-(Hydroxymethyl)-4,6-dioxo-3,4,7,8-tetrahydro-3H-cyclopenta[g]quinazoline 12

A 72 L, 3 neck flask was equipped with a magnetic stirrer, a N$_2$ inlet, a septum cap, and a type-J Teflon® covered thermocouple. The flask was purged with N$_2$ and charged with the benzyl ether 6 (800 gm, 2.50 mol, corrected for a wt % purity of 80%) and anhydrous dichloromethane (25 L). The resulting brown solution was cooled to −40° C., causing considerable precipitation. The resultant slurry was treated with a 1M solution of BCl$_3$ in CH$_2$Cl$_2$ (7.5 L, 7.5 mol). The rate of addition was controlled so that the internal reaction temperature did not rise above −30° C. The total time for the addition was approximately 45 minutes. After the addition was complete, the reaction was allowed to stir for 2 hours at −40° C. and monitored for completion by HPLC (st material Rt=8.8 min, product Rt=4.0 min). The reaction was cooled to −40° C. and quenched by the addition of a methanol (22 L)/triethylamine (3.5 L) solution. The temperature of the reaction rose to −20° C. during the addition. The reaction mixture was then allowed to warm to 20° C. overnight. The next day the batch was concentrated under reduced pressure to afford a greenish oil. The residual reaction solvents were chased with methanol (20 L) and dry HPLC grade acetonitrile (2×10 L). The resulting dry green solid (~3.7 kg) was taken onto the next step without purification.

2-(t-Butyldimethylsiloxymethyl)-4,6-dioxo-3,4,7,8-tetrahydro-3H-cyclopenta[g]quinazoline 7

A 22 L, 3 neck flask was equipped with an overhead stirrer, a N$_2$ inlet, and a type-J Teflon® covered thermocouple. The flask was purged with N$_2$ and charged with the crude alcohol 12 prepared above, acetonitrile (7 L) and triethylamine (1400 mL, 10.0 mol). The batch was cooled to ~10° C.-15° C. using a cold water bath. To the resulting yellow-green suspension was added solid TBDMSCl (1125 g, 7.50 mol), portionwise over ~20 minutes. The addition was mildly exothermic causing the internal reaction temperature to rise to ~20° C. After the addition was complete the reaction was stirred overnight at 20° C. under an atmosphere of N$_2$. The following morning the reaction was judged to be >95% complete by TLC or HPLC. The dark green reaction mixture was filtered through a plasticware filter pot (24"×11") prepacked with gravity grade silica gel (3 kg-slurried in acetonitrile) and a top and bottom layer of celite 21 (500 grams each). The filter pot was rinsed with acetonitrile (10 L, ACS grade) prior to adding the reaction mixture to the pot. Once the reaction mixture containing green solids was added, the filter pot was rinsed with acetonitrile (80 L, ACS grade), collecting 10 L cuts. The washing operation was monitored by TLC until no more product was detected in the washings. This was concentrated in vacuo to afford 2.2 kg of crude which needed to be purified further by silica gel chromatography. 8 kg of flash grade silica gel was slurry packed in CH$_2$Cl$_2$ onto an 8"×48" column. The material was loaded with ~1.5 L of CH$_2$Cl$_2$. 25 fractions were collected in total as 4 L cuts per fraction. Fractions 1-10 were 100% CH$_2$Cl$_2$ and fractions 11-25 were 5% EtOAc/CH$_2$Cl$_2$. Fractions 5-9 are the bulk of the material, while fractions 10-15 were evaporated separately for re-chromatography. Fractions 5-9 containing the product and some higher and lower rf material were combined and concentrated to afford 444 gm of a green solid which was ~93% pure by weight % assay for an actual yield of 412 gm (48% yield over two steps). This material has a solubility in ethyl acetate of ~25 mg/ml and in 1:1 hexanes:ethyl acetate of 15 mg/ml. TLC analysis Rf=0.30 (50% EtOAc/hexanes). HPLC 10:90 to 90:10 CH$_3$CN:H$_2$O over 15 min. Hold at 90:10 for 2 min, 0.025% TFA Buffer, 1.5 mL/min, UV at 220 nm, Phenomenex Jupiter C18 column 4.6 mm×250 mm at 29° C.: (12.90 min, 92-93 A %) $^1$H NMR (CDCl$_3$, 300 MHz): 0.20 (s, 6H), 0.98 (s, 9H) 2.77-2.81 (m, 2H), 3.27-3.31 (m, 2H), 4.72 (s, 2H), 7.64 (s, 1H), 8.72 (s, 1H), 9.53 (br, 1H).

(R,S)-2-(t-Butyldimethylsiloxymethyl)-6-hydroxy-4-oxo-3,4,7,8-tetrahydro-3H-cyclopenta[g]quinazoline 13

A 22 L, 4 neck flask was equipped with an overhead stirrer, an N$_2$ inlet and a type-K Teflon® covered thermocouple. The flask was purged with N$_2$ and charged with the chromatographed ketone 7 (500 g, 1.45 mol) and ethanol (15 L). To the resulting yellow suspension was added solid sodium borohydride (71 g, 0.563 mol) in three portions over approximately 25 minutes. No immediate exotherm or excessive gas evolution was noted, however after one hour a mild exotherm to above room temperature was detected. A bath of cool water (15-20° C.) was placed under the flask to moderate the temperature and bring the reaction temperature to 23° C. After 20 minutes, a homogeneous solution had formed. At the end of three hours, the reaction was judged complete by TLC and HPLC. The solvent was removed in vacuo (bath temperature ~35° C.) and the residue was transferred to a separatory funnel with 5 L of ethyl acetate and washed twice with 3 L of a saturated $KH_2PO_4$ solution. The combined aqueous washes were back extracted with 3 L of ethyl acetate. The combined organic extracts were washed with 3 L of brine (2×) and dried over anhydrous sodium sulfate. Filtration and removal of the solvent in vacuo followed by a solvent flush with 2 L of hexanes afforded a light green solid which was triturated with hexane (1.5 L) at ambient temperature for 1-2 hours and filtered. After air drying overnight at 20° C. 458 grams of the desired alcohol as a light green solid was obtained (92%). The KF of this material typically showed a water content of 0.5% water by weight. TLC analysis Rf=0.20 (75% EtOAc/hexanes). HPLC 10:90 to 90:10 $CH_3CN:H_2O$ over 15 min. Hold at 90:10 for 2 min, 0.025% TFA Buffer, 1.5 mL/min, UV at 220 nm, Phenomenex Jupiter C18 column 4.6 mm×250 mm at 29° C.: (11.68 min, 98.0 A %)$^1$H NMR ($CDCl_3$, 300 MHz): 0.19 (s, 6H), 0.97 (s, 9H), 1.99 (d, 1H), 2.0-2.15 (m, 1H), 2.5-2.61 (m, 1H), 2.85-3.0 (m, 1H), 3.1-3.3 (m, 1H), 4.70 (s, 2H), 5.3-5.4 (q, 1H), 7.46 (s, 1H), 8.31 (s, 1H), 9.43 (br s, 1H).

(R)-2-(t-Butyldimethylsiloxymethyl)-6-hydroxy-4-oxo-3,4,7,8-tetrahydro-3H-cyclopenta[g]quinazoline 13R To a magnetically stirred two-phased mixture of dichloromethane (5 mL) and water (5 mL), was added the ketone (690 mg, 0.002 mol), sodium formate (680 mg, 0.010 mol), tetrabutylammonium bromide (64 mg, 0.0002 mol) and chloro[1R,2R)-TSDPEN](p-cymene) ruthenium(II) (25 mg, 0.00004 mol). The reaction mixture was stirred at room temperature for 48 hours. At this point, the reaction was analyzed by thin-layer chromatography and found to be complete. The reaction mixture was transferred to a separating funnel and ethyl acetate (25 mL) was added. The reaction mixture was washed sequentially with saturated sodium bicarbonate solution (2×15 mL), brine (20 mL) and then dried over anhydrous sodium sulfate (10 g). Filtration and removal of the solvent afforded a semi-solid. The semi-solid material was chromatographed on silica gel (7 gr) using a 75% ethyl acetate/hexane mixture (100 mL). The indanol (500 mg, 72% yield) was obtained as a white solid which conformed to the desired structure.

TLC analysis $R_f$=0.20 (75% EtOAc/hexanes). HPLC 10:90 to 90:10 $CH_3CN:H_2O$ over 15 min. Hold at 90:10 for 2 min, 0.025% TFA Buffer, 1.5 mL/min, UV at 220 nm, Phenomenex Jupiter C18 column 4.6 mm×250 mm at 29° C.: (11.68 min, 98.0 A %) $^1$H NMR ($CDCl_3$, 300 MHz): 0.19 (s, 6H), 0.97 (s, 9H), 2.0-2.15 (m, 1H), 2.4 (d, 1H), 2.5-2.61 (m, 1H), 2.85-3.0 (m, 1H), 3.1-3.3 (m, 1H), 4.70 (s, 2H), 5.3-5.4 (q, 1H), 7.44 (s, 1H), 8.31 (s, 1H), 9.43 (br s, 1H). Enantiomeric excess=98% t-Butyl (6RS)-4,N-((2-(t-butyldimethylsiloxymethyl)-4-oxo-3,4,7,8-tetrahydro-3H-cyclopenta[g] quinazolin-6-yl)-N-(prop-2-ynyl)amino)benzoate 14

A 15 L, 4 neck jacketed reactor was equipped with an overhead stirrer, an $N_2$ inlet, an $N_2$ outlet, and a type-K Teflon® covered thermocouple. A Huber Chiller was used to maintain the internal temperature, and was set for 10° C. (during the addition of the methanesulfonic anhydride). The flask was purged with $N_2$ and charged with isopropyl acetate (8 L). To the solvent was added indanol 7 (415 gm, 1.20 mol) and tert-butyl 4-(N-propargylamino)benzoate (887 gm, 3.84 mole). The brown suspension was vigorously stirred and triethylamine (711 ml, 5.11 mole) was added. The batch temperature was brought to about 17° C., just prior to charging methanesulfonic anhydride. To the suspension was added solid methanesulfonic anhydride (460 gm, 2.64 mole) in 5 equal portions. There was an exotherm to about 22° C. after each addition which was allowed to subside, and the internal temperature allowed to return to about 17-19° C. before the next charge of the anhydride. This required about 10-15 minutes for each addition of the anhydride. The reaction was allowed to stir at 20-25° C. for 30 minutes, and HPLC data confirmed the starting material had been consumed. At this point, the reaction was partitioned between water (4 L) and ethyl acetate (4 L). The layers were separated and the aqueous layer was re-extracted with ethyl acetate (4 L). The combined organic extracts were washed with saturated sodium bicarbonate solution (4 L), brine (4 L) and dried ($Na_2SO_4$). Removal of the solvent in vacuo afforded 1.3 kilograms of a thick brown liquid that solidified on standing. The crude material was slurry loaded as a methylene chloride solution (~2 L) onto 1.5 kilograms of flash grade silica gel and solvent stripped to a dry powder. This was loaded onto 8 kilograms of flash grade silica gel and was chromatographed using a gradient elution of 10% ethyl acetate/hexane increasing to 50% ethyl acetate/hexane (10%-30 L, 20%-40 L, 30%-40 L, 40%-40 L, 50%-50 L). The fractions containing clean product were combined and concentrated to afford 386 grams of desired material (92%, 85 by wt %, 328 g corrected yield, 48% corrected yield). TLC analysis Rf=0.18 (25% EtOAc/hexanes). HPLC 10:90 to 90:10 $CH_3CN:H_2O$ over 15 min. Hold at 90:10 for 2 min, 0.025% TFA Buffer, 1.5 mL/min, UV at 220 nm, Phenomenex Jupiter C18 column 4.6 mm×250 mm at 29° C.: (18.68 min, 98.0%, des-propargyl Rt=17.1 min)$^1$H NMR ($CDCl_3$, 300 MHz): 0.18 (s, 6H), 0.97 (s, 9H), 2.2 (t, 1H, J=2.4 Hz), 2.3-2.42 (m, 1H), 2.55-2.65 (m, 1H), 2.95-3.1 (m, 1H), 3.15-3.3 (m, 1H), 3.9 (ABqd, 2H, J=2.4 Hz), 4.7 (s, 2H), 5.6-5.7 (t, 1H), 6.96 (d, 2H, J=9 Hz), 7.5 (s, 1H), 7.92 (d, 2H, J=9 Hz), 8.13 (s, 1H), 9.45 (br s, 1H).

t-Butyl (6S)-4,N-((2-(t-butyldimethylsiloxymethyl)-4-oxo-3,4,7,8-tetrahydro-3H-cyclopenta[g]quinazolin-6-yl)-N-(prop-2-ynyl)amino)benzoate 14S The preparative chiral separation was done on a CHIRAL-PAK AD® column with a 1:1 mixture of hexane/isopropanol as eluent. The temperature during the resolution was 25° C. and the UV detection wavelength was 330 nm. Using these conditions, 1715 grams of racemic compound 14 were separated. The desired enantiomer 14S (781.2 g) was the first eluting peak and was obtained in 99.6% e.e and 95.3% purity. $[\alpha]_D^{25}$ (c=1.015; $CHCl_3$)-75.8°.

16S)-4,N-((2-(Hydroxymethyl)-4-oxo-3,4,7,8-tetrahydro-3H-cyclopenta[g]quinazolin-6-yl)-N-(prop-2-ynyl)amino)benzoic acid 4

A 2 L, 3 neck flask was equipped with an overhead stirrer, an addition funnel, a $N_2$ inlet and a type-K Teflon® covered thermocouple. An empty secondary containment vessel was placed under the reaction vessel. The flask was purged with $N_2$ and charged with acetonitrile (1000 ml) and the protected quinazolinone 14S (112 gm, 0.2 mol), as a solid, in one portion. To the resulting slurry at room temperature was added methanesulfonic acid (43 mL, 0.66 mole) dropwise over approximately 30 minutes. After approximately one-half of the methanesulfonic acid was added, a yellow solution formed. The reaction exothermed approximately 6° C. during the addition. After approximately three hours a precipitate started to form. The reaction was allowed to stir overnight at room temperature. In the morning, a thick precipitate had formed. The reaction was analyzed by HPLC and found to be complete. The reaction mixture was poured into a mechanically stirred 1:1 ice/water mixture (4 L). The pH of the slightly turbid mixture was approximately 1.3. The pH of the solution was brought to pH 5 (+/−0.1, pH meter) with the addition of 6N NaOH (~115 mL). A beige solid precipitated at this point. The mixture was allowed to stir at room temperature for 1 hour. The temperature of the mixture was approximately 8° C. at this point. The solid was filtered, washed with 500 mL of water and then with 500 mL of a 1:1 mixture of hexane/isopropanol. The wet cake was placed into a vacuum drying oven at 70° C. overnight. Obtained 73.2 grams of the desired acid (94%) which was 95% pure by HPLC. The water content of the solid was found to be 0.9% as determined by Karl Fischer analysis. HPLC 10:90 to 90:10 $CH_3CN:H_2O$ over 15 min. Hold at 90:10 for 2 min, 0.025% TFA Buffer, 1.5 mL/min, UV at 220 nm, Phenomenex Jupiter C18 column 4.6 mm×250 mm at 29° C.: (Rt=8.21 min). The material was >99% EE. $^1$H NMR (DMSO-$d_6$, 300 MHz): 2.16-2.24 (m, 1H), 2.4-2.58 (m, 1H), 2.9-3.1 (m, 1H), 3.13 (t, 1H, J=2.4 Hz), 3.1-3.25 (m, 1H), 3.83, 4.07 (ABqd, 1H, 1H, $J_1$=18.9 Hz, $J_2$=2.4 Hz), 4.36 (s, 2H), 5.5-5.7 (br, 1H), 7.02 (d, 2H, J=9 Hz), 7.53 (s, 1H), 7.79 (d, 2H, J=9 Hz), 7.80 (s, 1H,). C, H, N Theory: % C, 67.86; % H, 4.92; % N, 10.79. Found: % C, 67.88; % H, 4.84; % N, 10.54.

5-(t-Butoxyacetamido)-6-bromoindan-1-one 15

A flame-dried 10 L, 4 necked round bottom flask was equipped with a mechanical stirrer, a reflux condenser, a thermo-socket and a nitrogen inlet. The flask was charged with tert-butoxyacetic acid (250 g, 1.89 mol, 1 eq) and dry dichloromethane (6.25 L). The flask was cooled in an ice-salt mixture to −5-0° C. To the solution was added diethyl chlorophosphate slowly over a period of 15 min (816 g, 4.72 mol, 2.5 eq) followed by the dropwise addition of triethylamine (478 g, 4.73 mol, 2.5 eq) over a period of 30 minutes with the temperature of the reaction not exceeding 25° C. during the addition. The stirred reaction mixture was gradually allowed to warm to 25-30° C. for one hour and then 5-amino-6-bromo-1-indanone (282.5 g, 1.25 mol, 0.66 eq) and triethylamine (478 g, 4.73 mol, 2.5 eq) were added. The reaction was refluxed for 24 hours and an aliquot was removed and analyzed by HPLC. The reaction was found to be complete (Starting material <0.5%). The solvent was removed on the rotary evaporator in vacuo affording a brown viscous residue. To the residue was added 4.7 L of a 20% methanol/water mixture. The sticky mixture was stirred with a mechanical stirrer for 20 hours. A free flowing solid formed which was filtered off and washed with 500 ml of water and dried at 55° C. in vacuo for 8 hours. 378 g (89%) of the desired tert-butoxyacetanilide was obtained as a tan powder after drying.

The material was analyzed and found to be 101 weight % pure by comparison to an analytical standard of known purity. HPLC 10:90 to 90:10 $CH_3CN: H_2O$ over 15 min. Hold at 90:10 for 2 min, 0.025% TFA Buffer, 1.5 mL/min, UV at 220 nm, Phenomenex Jupiter C18-3 column 4.6 mm×250 mm at 29° C.: (12.6 min, 95 A %). The product displayed the following physicochemical properties: $^1$H NMR (CDCl$_3$, 300 MHz): 1.35 (s, 9H), 2.65-2.75 (m, 2H), 3.12-3.16 (m, 2H), 4.07 (s, 2H), 7.96 (s, 1H), 8.7 (s, 1H), 9.55 (br, 1H).

5-(t-Butoxyacetamido)-6-cyanoindan-1-one 16

A 5 L, 4 necked round bottom flask was equipped with a mechanical stirrer, a argon inlet, a solid addition funnel, and a reflux condenser. The flask was charged with 2-tert-butoxy acetamide 15 (370 g, 1.08 mol, 1 eq) and N,N-dimethyl acetamide (2.3 L). Argon was bubbled through the resulting dark viscous solution for 30 minutes. After degassing, tetrakis (triphenylphosphine) palladium (50.3 g, 0.043 mol, 0.04 eq) was added to the stirring solution. The resulting slurry was then heated to 85° C. and was treated with solid $Zn(CN)_2$ (75.3 g, 0.541 mol, 0.59 eq) added in 5 aliquots over a period of 50 minutes. The reaction was stirred at 90° C. for 2 hours. At that time the reaction was judged to be completed (by IPC-HPLC) and was allowed to cool to room temperature and stirred 12 hours at ambient temperature under an argon atmosphere. The reaction mixture was slowly poured into 7.5 L of ice-water resulting in the formation of a yellow precipitate. The yellow solid was stirred further 3 hours and then collected by Buchner filtration and was rinsed with water (2.5 L). The solids were stirred with 1.8 L of 20% isopropanol/hexane for 1 hour and then collected by Buchner filtration followed by a washing with 750 mL of hexane. The solids were dried in a vacuum oven at 50° C. until a constant weight was reached (20 hours). Obtained 310 g (99.6% yield) of a yellow powder. This material was used directly in the next step without further purification.

The material was analyzed and found to be 78.5 weight % pure by comparison to an analytical standard of known purity. HPLC 10:90 to 90:10 $CH_3CN:H_2O$ over 15 min. Hold at 90:10 for 2 min, 0.025% TFA Buffer, 1.5 mL/min, UV at 220 nm, Phenomenex Jupiter C18-3 column 4.6 mm×250 mm, 5 μm at 29° C.: (10.97 min, 91.8 A %)$^1$H NMR (CDCl$_3$, 300 MHz): 1.43 (s, 9H), 2.73-2.77 (m, 2H), 3.21-3.25 (m, 2H), 4.09 (s, 2H), 8.00 (s, 1H), 8.76 (s, 1H), 9.60 (bs, 1H).

2-(t-Butoxymethyl)-4,6-dioxo-3,4,7,8-tetrahydro-3H-cyclopenta[g]quinazoline 17

A 5 L, four necked round bottom flask was equipped with a mechanical stirrer, and an addition funnel topped with a $N_2$ inlet. The flask was purged with $N_2$ and charged with 2-tert-butoxy-N-(6-cyano-1-oxoindan-5-yl) acetamide 16 (200 g, 0.699 mol, 1 eq), ethanol (1.6 L) and water (400 mL). Stirring was initiated and the resulting suspension was cooled to 0-5° C. Hydrogen peroxide (30% w/v, 240 mL, 2.09 mol, 3 eq) was added drop wise over a thirty minute period to maintain the internal temperature at not more than 5° C. A slight exotherm was noted during the addition. The mixture was allowed to stir at this temperature for thirty minutes and then 6N sodium hydroxide solution (194 mL, 1.12 mol, 1.6 eq) was added drop wise over approximately 30 minutes. The temperature of the reaction was kept between 0-5° C. during the addition. After the addition was complete, the reaction was allowed to stir for twenty minutes at 0° C. and was then allowed to warm to room temperature, whereupon a spontaneous exotherm to approximately 60° C. occurred. Once the temperature of the reaction had subsided to approximately 40° C., it was monitored for completion by IPC-HPLC. At this point, the reaction was complete. The reaction mixture was cooled to room temperature placed on an ice-bath and sodium bisulfite (148 g, 1.4 mol, 2 eq) was added in one portion. When the exotherm had subsided, the reaction mixture was poured into 12

L of a 1:1 ice-water mixture. The pH of the mixture was adjusted from approximately 6 (initial pH) to 4 with 85% phosphoric acid (50 mL) using a calibrated pH meter. The mixture was concentrated under reduced pressure until most ethanol was removed, further water (1 L) was added, and the mixture was allowed to stand for several hours. The precipitate was collected by filtration, washed with water (2 L) and dried at 50° C. for 8 hours. Then the solid was further stirred with 20% isopropanol/hexanes (8 L) for 2 hours. The solid was collected on a Buchner funnel and finally washed with hexanes (1 L), sucked dry and placed in a vacuum drying oven at 60° C. and dried to constant weight. 114 g (57%) of the desired pyrimidinone 17 was obtained as a greenish yellow powder.

The material was analyzed and found to be 82.5 weight % pure by comparison to an analytical standard of known purity. HPLC 10:90 to 90:10 $CH_3CN:H_2O$ over 15 min. Hold at 90:10 for 2 min, 0.025% TFA Buffer, 1.5 mL/min, UV at 220 nm, Phenomenex Jupiter C18 column 4.6 mm×250 mm at 29° C.: (8.09 min, 93.3 A %) $^1$H NMR ($CDCl_3$, 300 MHz): 1.35 (s, 9H), 2.77-2.81 (m, 2H), 3.29-3.31 (m, 2H), 4.5 (s, 2H), 7.64 (s, 1H), 8.7 (s, 1H), 9.65 (bs, 1H).

(R,S)-2-(t-Butoxymethyl)-6-hydroxy-4-oxo-3,4,7,8-tetrahydro-3H-cyclopenta[g]quinazoline 18

A 10 L, four necked round bottom flask was equipped with a mechanical stirrer and a $N_2$ inlet. The flask was cooled in an ice bath to 10-15° C. (temperature of the bath is checked with a thermometer, internal temperature was maintained between 15-20° C.). The flask was purged with $N_2$ and charged with 2-(t-butoxymethyl)-4,6-dioxo-3,4,7,8-tetrahydro-3H-cyclopenta[g]quinazoline 17 (250 g, 0.874 mole, 1 eq) and ethanol (5 L). To the resulting yellow suspension was added solid sodium borohydride (43 g, 1.22 mol, 1.4 eq) in five portions over a 15 minute period. After 2 hours, a homogeneous solution was obtained, and the reaction was judged complete by IPC-HPLC. The solvent was removed in vacuo (bath temperature less than 50° C.) to near dryness. To the dark residue was added 1.25 L of a 0.5M $KH_2PO_4$ solution followed by water (7.5 L). The pH of the mixture was adjusted from approximately 8 (initial pH) to 4 with 85% phosphoric acid (~50 mL) using a calibrated pH meter. A solid precipitated formed, which was allowed to stir for 20 hours at 5° C. to complete the precipitation process. The solid was filtered, washed with water (2 L), and dried in a vacuum oven at 50° C. until the moisture content was less than 1%. Obtained 236 grams (90%) of the desired indanol 18 as a greenish-yellow powder in 96.6 A % purity.

The material was analyzed and found to be 77 weight % pure by comparison to an analytical standard of known purity. HPLC 10:90 to 90:10 $CH_3CN:H_2O$ over 15 min. Hold at 90:10 for 2 min, 0.025% TFA Buffer, 1.5 mL/min, UV at 220 nm, Phenomenex Jupiter C18 column 4.6 mm×250 mm at 29° C.: (7.08 min, 96.6 A %) $^1$H NMR ($CDCl_3$, 300 MHz), 1.30 (s, 9H), 2.05-2.15 (m, 1H), 2.5-2.61 (m, 1H), 2.85-3.0 (m, 1H), 3.1-3.3 (m, 1H), 4.48 (s, 2H), 5.34 (t, 1H, J=4.8 Hz), 7.45 (s, 1H), 8.30 (s, 1H), 9.54 (bs, 1H).

t-Butyl (6RS)-4,N-((2-(t-butoxymethyl)-4-oxo-3,4,7,8-tetrahydro-3H-cyclopenta[g]quinazolin-6-yl)-N-(prop-2-ynyl)amino)benzoate 19

A 20 L, 3 neck round-bottom flask was equipped with a mechanical stirrer, a reflux condenser and argon inlet. The flask was purged with argon and (R,S)-2-(t-butoxymethyl)-6-hydroxy-4-oxo-3,4,7,8-tetrahydro-3H-cyclopenta[g]quinazoline 18 (240 g, 0.833 mol, 1 eq) and ethyl acetate (12 L) were charged to the flask. Heating was begun and the mixture was heated to reflux until a clear solution was obtained. The reaction mixture was allowed to cool to room temperature. At this point, triethylamine (566 mL, 3.99 mol, 4.8 eq) and tert-butyl propargylaminobenzoate (614 g, 2.66 mol, 3.2 eq) were added followed by addition of methane sulfonic anhydride (362.4 g, 2.08 mol, 2.5 eq) in five aliquots in 15 min intervals, when the internal temperature had returned to 20° C. There was an exotherm to about 28° C. after each addition. The reaction was allowed to stir at 20-25° C. for 12 hours, and HPLC IPC data confirmed the starting indanol had been completely consumed. The reaction mixture was poured into a stirred solution of 0.5M potassium dihydrogen phosphate solution (9.6 L). The layers were separated and the aqueous layer was re-extracted with ethyl acetate (4.8 L). The organic layers were combined and washed with 4.8 L of brine and dried over anhydrous sodium sulfate. Removal of the solvent in vacuo afforded approximately 800 g of a thick brown liquid. To the crude materials was added 2.5 L of methanol and the mixture was stirred vigorously for 3 hours for complete precipitation. The solid was collected by filtration and washed with 500 ml of cold methanol. The solid obtained was dried in vacuo for 4 hours to afford 180 grams of the desired material (58% uncorrected).

The filtrate was concentrated and the crude material was pre-adsorbed onto 500 g silica gel (60-120 mesh) and solvent stripped to get a dry powder. This was dry loaded onto 2 Kg silica gel (60-120 mesh) and was chromatographed using a gradient elution of 5% ethyl acetate/hexanes increasing to 40% ethyl acetate/hexanes. The fractions containing clean product were combined and concentrated to afford 55 g of the desired material (17.7% uncorrected).

The materials obtained from crystallization and column chromatography were combined and triturated with isopropyl alcohol (460 ml) and hexanes (2.3 L). The slurry obtained was stirred 60 min and the solid was collected and washed with 5% isopropyl alcohol-hexane mixture (500 ml). The wet material was dried in vacuo for 8 hours to afford 205 g (66.3%) of desired quality product 19.

This material was analyzed and found to be 98.2 weight % pure by comparison to an analytical standard of known purity. HPLC 10:90 to 90:10 $CH_3CN:H_2O$ over 15 min. Hold at 90:10 for 2 min, 0.025% TFA Buffer, 1.5 mL/min, UV at 220 nm, Phenomenex Jupiter C18 column 4.6 mm×250 mm at 29° C.: (14.6 min, 98.3 A %)$^1$H NMR ($CDCl_3$, 300 MHz): 1.32 (s, 9H), 1.58 (s, 9H), 2.19-2.2 (m, 1H), 2.34-2.41 (m, 1H), 2.58-2.63 (m, 1H), 3.02-3.23 (m, 1H), 3.24-3.3 (m, 1H), 3.9 (dd, 2H), 4.5 (s, 2H), 5.66-5.69 (t, J=8.1 Hz, 1H), 6.96 (d, 2H, J=11.4 Hz), 7.54 (s, 1H), 7.94 (d, 2H, J=11.4 Hz), 8.13 (s, 1H), 9.59 (bs, 1H). $^{13}$C NMR ($CDCl_3$): 27.5, 28.4, 30.0, 30.5, 36.0, 61.3, 63.8, 72.0, 75.5, 80.1, 80.8, 112.7, 120.7, 121.3, 122.5, 123.1, 131.3, 141.1, 149.2, 151.2, 151.4, 154.0, 161.5, 166.0.

t-Butyl (6S)-4,N-((2-(t-butoxymethyl)-4-oxo-3,4,7,8-tetrahydro-3H-cyclopenta[g]quinazolin-6-yl)-N-(prop-2-ynyl)amino)benzoate 19S A simulated moving bed chromatographic apparatus with 8 columns of approximately 10 cm in length, and 5 cm internal diameter, was charged with 800 g of (S,S)-Whelk-O1 resin and equilibrated with 40% dichloromethane, 60% methyl tert-butyl ether solvent mixture. Racemic t-butyl (6R, S)-4,N-((2-(t-butoxymethyl)-4-oxo-3,4,7,8-tetrahydro-3H-cyclopenta[g]quinazolin-6-yl)-N-(prop-2-ynyl)amino)benzoate, 19, (800 g) was fed into the apparatus as a 16 g/L solution in 40% dichloromethane, 60% methyl tert-butyl ether at a rate of 40.5 ml/min, and the apparatus was run at ambient temperature with a solvent feed rate of 380 mL/minute, and an averaged operating pressure of 26 bars. This separation was repeated in total 11 times on a total of 9.0 kg of racemic 19, to give 19S (4.4 kg, 97.8%) as an amorphous light yellow solid, with a purity of >98% A, and an enantiomeric excess of 99.8%.

A 50 liter glass-jacketed reactor was sequentially charged with amorphous 19S (2.30 kg) and n-heptane (21.50 kg). The reaction mixture was stirred and allowed to warm to 65° C. Isopropyl alcohol (6.91 kg) was slowly charged to the reaction mixture, while maintaining the internal temperature at approximately 65° C. Once a homogeneous mixture was obtained, the solution was allowed to cool to 0° C. over a period of 8 hours. The resultant slurry was filtered and washed with cold n-heptane (2.30 kg), followed by a second chase with cold n-heptane (2.30 kg), and the solids were dried at 45° C. under high vacuum to give crystalline 19S (1.93 kg, 83.9%) as a fine white to off-white solid, mp 171° C., with 99.93% A purity by hplc analysis. $[\alpha]_D$ 1% w/v in $CH_2Cl_2$ at 25° C.-100.3°.

(6S)-4,N-((2-(Hydroxymethyl)-4-oxo-3,4,7,8-tetrahydro-3H-cyclopenta[g]quinazolin-6-yl)-N-(prop-2-ynyl)amino)benzoic acid 4 t-Butyl (6S)-4,N-((2-(t-butoxymethyl)-4-oxo-3,4,7,8-tetrahydro-3H-cyclopenta[g]quinazolin-6-yl)-N-(prop-2-ynyl) amino)benzoate (19S) (15.0 g, 0.03 Mol) was added continuously through a powder funnel to a solution of 70 wt % methanesulfonic acid in water (100 ml, 9.8N, 0.98 Mol) under nitrogen at ambient temperature with mechanical stirring. No exotherm was observed. The resulting suspension, with the solid floating on top of the solution gradually cleared after stirring for about one hour at ambient temperature. The resulting dark amber solution was agitated for four hours, when in process hplc showed the reaction was >99% complete. The reaction mixture was then charged into a mechanically stirred aqueous solution of NaOH (500 ml, 2.0 N, 1000 mmol) at 5° C. over 15 minutes, while maintaining the internal temperature below 20° C. An off-white solid precipitated out during the addition. The reaction vessel was rinsed into the quench vessel with 5.0 ml of 70 wt % aqueous MsOH. The pH at the end of the addition was about 10.0. Using an aqueous solution of 1.0 N MsOH (~30 mL) and a calibrated pH meter, the pH of the resulting mixture was adjusted to pH 5. The resulting suspension was stirred at 5° C. for five hours to allow the pH to stabilize at around 5.0 (±0.1). During this time the solid became granular. The solid was filtered, and washed with water (2×20 ml). The wet cake was dried at 40° C. in a draft oven in vacuo with an air-bleed for 12 hours to give acid 4 (11.0 g, 91%) as a light beige solid. Its purity was 99 A % as determined by HPLC, (10:90 to 90:10 $CH_3CN:H_2O$ over 15 min. Hold at 90:10 for 2 min, 0.025% TFA Buffer, 1.5 mL/min, UV at 220 nm, Phenomenex Jupiter C18 column 4.6 mm×250 mm at 29° C.: (8.21 min) the water content was found to be 3.0 wt % as determined by Karl Fischer analysis, and the enantiomeric excess was >99% as determined by chiral HPLC. $^1$H NMR (DMSO-$d_6$, 300 MHz): 2.14-2.32 (m, 1H), 2.44-2.58 (m, 1H), 2.93-3.08 (m, 1H), 3.10-3.25 (m, 2H), 3.84, 4.08 (ABqd, 1H, 1H, $J_1$=18.9 Hz, $J_2$=2.4 Hz), 4.38 (s, 2H), 5.78 (t, 1H, J=7.8 Hz), 7.03 (d, 2H, J=8.8 Hz), 7.55 (s, 1H), 7.82 (d, 2H, J=8.80 Hz), 7.83 (s, 1H).

O-t-Butyl 4-(trifluoroacetamido)benzoate 21

A 3 L, four necked round bottom flask was equipped with a mechanical stirrer and a $N_2$ inlet, and placed on an ice-bath. To a 0° C. solution of tert-butyl 4-aminobenzoate (250 g, 1.29 mol, 1 eq) in pyridine (750 mL) was slowly added trifluoroacetic anhydride (406 g, 1.94 mol, 1.5 eq) at a rate which maintained the internal temperature below 5° C. The mixture was warmed to room temperature, stirred for 24 hours and poured over a mixture of ice (4 Kg) and 1M $KH_2PO_4$ (8.5 L). The pH of the resulting mixture was 5-6 as checked by calibrated pH meter. This mixture was extracted with EtOAc (3×4 L). The combined EtOAc extracts were washed with 1 M aqueous citric acid (2×3 L), saturated $NaHCO_3$ (2×5 L), saturated sodium chloride solution (2.5 L), dried over $Na_2SO_4$, filtered and evaporated to give a off-white solid, and dried in vacuo at 25-30° C. for 8 hours to give 374 g of the product (100% yield).

The material was analyzed and found to be 99.1 area % pure. HPLC 10:90 to 90:10 $CH_3CN:H_2O$ over 15 min. Hold at 90:10 for 2 min, 0.025% TFA Buffer, 1.5 mL/min, UV at 220 nm, Phenomenex Jupiter C18 column 4.6 mm×250 mm at 29° C.: (13.22 min, 99 A %) $^1$H NMR (300 MHz; $CDCl_3$) δ 1.61 (s, 9H), 7.64 (d, J=8.7 Hz, 2H), 7.97 (bs, 1H), 8.03 (d, J=8.7 Hz, 2H).

O-t-Butyl 4-(N-propargylamino)benzoate 5

A 5 L, four necked round bottom flask was equipped with a mechanical stirrer, thermo-socket and a $N_2$ inlet. A mixture of the intermediate 6 (370 g, 1.28 mol, 1 eq), propargyl bromide (80% solution in toluene, 380 g, 2.56 mol, 2 eq), $K_2CO_3$ (530 g, 3.84 mol, 3 eq) and DMF (2.3 L) was stirred for 24 hours at 40° C., cooled to 0-5° C. and water (10 L) was added. The resulting mixture was stirred for 8 hours and the resulting solid was collected by filtration, washed with water and air dried to give 290 g of the product (% yield 100). The tan solid was further triturated with 2% ethyl acetate/hexanes mixture to improve the purity (250 g, 84.4%).

The material was analyzed and found to be 98.7 area % pure. HPLC 10:90 to 90:10 $CH_3CN:H_2O$ over 15 min. Hold at 90:10 for 2 min, 0.025% TFA Buffer, 1.5 mL/min, UV at 220 nm, Phenomenex Jupiter C18 column 4.6 mm×250 mm at 29° C.: (12.62 min, 98.7 A) $^1$H NMR (300 MHz; $CDCl_3$) δ 1.58 (s, 9H), 2.24 (t, J=2.4 Hz, 1H), 4.0 (dd, J=2.4 Hz, 2H), 4.23-4.31 (m, 1H), 6.64 (d, J=9.0 Hz, 2H), 7.86 (d, J=9.0 Hz, 2H).

The invention claimed is:

1. A process for producing a cyclopentaquinazoline from a 5-amino-6-haloindanone comprising the steps of:
    (a) acylation of the 5-amino group;
    (b) cyanide displacement of the 6-halo group;
    (c) hydrolysis of the nitrile group produced in step (b); and
    (d) cyclisation of a 5-(N-acylamino)-6-amidoindanone to form a cyclopentaquinazoline ring system; and
    (e) reduction of the indanone keto group to produce an indanol.

2. A process according to claim 1, wherein (a) acylation of the 5-amino group comprises reaction of a 5-aminoindanone compound with an acylating agent.

3. A process according to claim 2 wherein the acylating agent is generated in situ by reaction of a carboxylic acid with a coupling agent.

4. A process according to claim 3 wherein the carboxylic acid is a carboxylic acid of formula $R^1CO_2H$, wherein $R^{1'}$ is selected from $R^1$ or a protected form thereof, and wherein $R^1$ is independently selected from hydrogen, amino, $C_{1-4}$alkyl, $C_{1-4}$-alkoxy, fluoro$C_{1-4}$alkyl, hydroxy$C_{1-4}$alkyl, or protected hydroxy$C_{1-4}$alkyl.

5. A process according to claim 3, wherein the acylating agent is a mixed phosphoric anhydride generated in situ by reaction of the carboxylic acid with a chlorophosphate ester.

6. A process according to claim 1, wherein (b) cyanide displacement of the 6-halo group comprises displacement of the 6-halo group with a cyanide nucleophile selected from zinc cyanide, potassium cyanide, sodium cyanide, and cuprous cyanide, optionally in the presence of a catalyst.

7. A process according to claim 6, wherein the catalyst is a palladium or nickel catalyst, complexed to a triarylphosphine or bidentate bisphosphine ligand.

8. A process according to claim 6, wherein the catalyst is a palladium$^0$ species complexed to a phosphine, such as tetrakis (triphenylphosphine) palladium.

9. A process according to claim 1, wherein (c) hydrolysis of the nitrile group produced in step (b) comprises conversion of the 6-nitrile produced in the cyanation step to an amide.

10. A process according to claim 9, wherein hydrolysis comprises treatment with acid.

11. A process according to claim 10, wherein hydrolysis comprises treatment with formic acid in the presence of magnesium sulfate.

12. A process according to claim 9, wherein hydrolysis comprises treatment with hydrogen peroxide.

13. A process according to claim 12, wherein hydrolysis comprises treatment with hydrogen peroxide and potassium carbonate in aqueous ethanol.

14. A process according to claim 1, wherein (d) cyclisation of a 5-(N-acylamino)-6-amidoindanone to than a cyclopentaquinazoline ring system comprises treatment of said 5-(N-acylamino)-6-amidoindanone with a base.

15. A process according to claim 14, wherein the base is a solution of an alkali metal alkoxide in a $C_{1-4}$ alkyl alcohol.

16. A process according to claim 15, wherein the base is a solution of an alkali metal alkoxide in the corresponding alcohol.

17. A process according to claim 1, wherein (d) cyclisation of a 5-(N-acylamino)-6-amidoindanone to form a cyclopentaquinazoline ring system occurs spontaneously during step (c) hydrolysis of the nitrile group.

18. A process according to claim 17, wherein steps (c) and (d) comprise sequential addition of hydrogen peroxide and aqueous sodium or potassium hydroxide to a mixture of the 5-acylamino-6-cyanoindan-1-one in an aqueous alcohol, the mixture then being allowed to warm and spontaneously exotherm, to form a cyclopentaquinazoline ring system.

19. A process to according to claim 15, further comprising purification of the crude cyclopentaquinazoline produced by crystallization of the material from an isopropanol/hexanes mixture.

20. A process according to claim 18, wherein (e) reduction of the indanone keto group to produce an indanol comprises treatment of an indanone with a hydride based reducing agent.

21. A process according to claim 20, wherein the reducing agent is sodium borohydride.

22. A process according to claim 1, further comprising a step of: (f) coupling of an amine nucleophile to the indan-1-ol produced in step (e).

23. A process according to claim 22, wherein coupling comprises conversion of the hydroxy group of the indanol into a leaving group, followed by reaction with an amine nucleophile.

24. A process according to claim 23, wherein conversion comprises reaction of the indanol with methanesulfonic anhydride, and treatment with an amine nucleophile.

25. A process according to claim 24, wherein conversion comprises mixing the indanol, the amine nucleophile and a base, in a solvent of low ionic power, and addition of the methanesulfonic anhydride to this mixture.

26. A process according to claim 25, comprising mixing the indanol, the amine nucleophile and a tertiary amine base in a solvent of low ionic power, and adding methanesulfonic anhydride in 4-8 equal portions, with 10-30 minutes between each addition; wherein the amine nucleophile is used in an amount of about 2.5-3.5 molar equivalents, the tertiary amine base is used in an amount of about 4-6 molar equivalents, and methanesulfonic anhydride is used in an amount of about 2-3 molar equivalents; and wherein the reaction temperature is in the range of 10-30° C.

27. A process according to claim 22, wherein the amine nucleophile is an amine of general formula (XV):

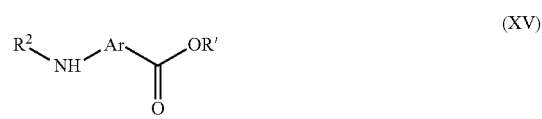

wherein $R^2$ is independently selected from hydrogen, $C_{1-4}$alkyl, $C_{3-4}$alkenyl, $C_{3-4}$alkynyl, hydroxy-$C_{2-4}$alkyl, halo$C_{2-4}$alkyl or cyano$C_{1-4}$-alkyl;

Ar is independently selected from $C_{5-20}$ arylene, optionally substituted on the ring with one or two substituents selected from halogen, hydroxy, amino, nitro, cyano, trifluoromethyl, and $C_{1-4}$alkoxy; and $R^1$ is hydrogen, or a protecting group.

28. A process according to claim 22, wherein the product is purified by crystallization from a suitable solvent.

29. A process according to claim 1, further comprising a step of: (g) chromatographic resolution.

30. A process according to claim 29, wherein (g) chromatographic resolution is carried out on the product of step (f) coupling.

31. A process according to claim 29, wherein chromatographic resolution comprises conventional column chromatography at low, medium, or high pressure, supercritical fluid chromatography or continuous multi column chromatography such as Simulated Moving Bed (SMB), with a chiral resin as stationary phase.

32. A process according to claim 31 wherein the chiral stationary phase is selected from Pirkle type resins such as (S,S) Whelk-O1, (R,R) Whelk-O1 and amylose or cellulose based chiral resin such as Chiralpak AD.

33. A process according to claim 29, wherein chromatographic resolution comprises elution with a solvent or a mixture of solvents selected from a linear or cyclic hydrocarbon selected from C6 to C8 such as hexane or n-heptane and a lower alcohol (methanol, ethanol, isopropanol, t-butanol), acetonitrile/lower alcohol (methanol, ethanol, isopropanol, t-butanol) mixtures and dichloromethane/methyl t-butyl ether mixtures.

34. A process according to claim 29, further comprising a crystallization step following the chromatographic resolution, to increase the chemical purity of the product obtained from the column, and to convert it to a crystalline form if it was obtained in amorphous form from the chromatography.

35. A process according to claim 34, whereby crystallization comprises crystallisation from a solvent system selected from isopropanol, isopropanol/heptane and isopropanol/hexanes mixtures.

36. A process according to claim 1, further comprising at least one step of protection, deprotection, or protecting group exchange.

37. A process according to claim 4, further comprising the step of a protecting group exchange comprising removal of a protecting group on $R^1$ and replacement with another protecting group.

38. A process according to claim 4, further comprising the step of deprotection, wherein a protecting group on $R^1$ and the protecting group R' are removed in a single step after resolution, and wherein the cyclopentaquinazoline is N-(2-(protected)cyclopentaquinazol-4-on-6-yl)aminoarylcarboxylate ester 6S-(VIIIa):

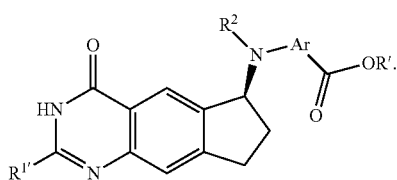

39. A process according to claim 38 wherein said protecting groups on are removed by treatment of compound 6S-(VIIIa) with a strong non-nucleophilic acid in a suitable organic solvent, at or below 25° C.

40. A process according to claim 39 whereby the strong non-nucleophilic acid used is methanesulfonic acid.

41. A process according to claim 40 wherein the methanesulfonic acid also acts as the solvent for the reaction.

42. A process according to claim 41 wherein the methanesulfonic acid is at a concentration of 70 wt % in water, and the initial temperature is in the 20-25° C. range.

43. A process according to claim 40 wherein the compound 6S-VIIIa,
where R'=H, is subjected to an isolation procedure comprising:
pouring the reaction mixture into ice and/or cold dilute sodium or potassium hydroxide, such that the final pH of the mixture is equal to or greater than 10;
addition of dilute methanesulfonic acid until the pH of the suspension is stabilized at 5;
stirring until the precipitate is granular;
collecting the material by filtration or centrifugation; washing with water; and drying.

44. A method of synthesis of a cyclopentaquinazoline compound, comprising
chromatographic resolution formula (VIIIa)

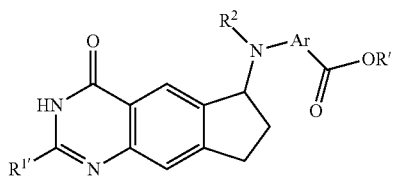

wherein $R^{1'}$ is selected from $R^1$ or a protected form thereof, and wherein $R^1$ is independently selected from hydrogen, amino, $C_{1-4}$alkyl, $C_{1-4}$-alkoxy, fluoro$C_{1-4}$alkyl, hydroxy$C_{1-4}$-alkyl, or protected hydroxy$C_{1-4}$alkyl,
wherein $R^2$ is independently selected from hydrogen, $C_{1-4}$alkyl, $C_{3-4}$alkenyl, $C_{3-4}$-alkynyl, hydroxy-$C_{2-4}$ alkyl, halo$C_{2-4}$-alkyl or cyano$C_{1-4}$alkyl;
Ar is independently selected from $C_{5-20}$ arylene, optionally substituted on the ring with one or two substituents selected from halogeno, hydroxy, amino, nitro, cyano, trifluoromethyl, $C_{1-4}$alkyl and $C_{1-4}$-alkoxy; and R' is hydrogen, or a protecting group;
into its enantiomers:

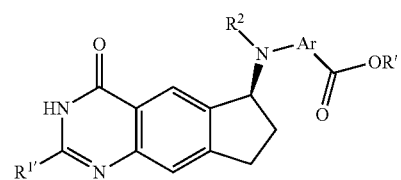

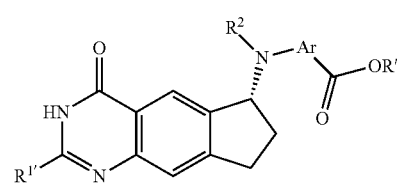

45. A method for the synthesis of amines of general formula:

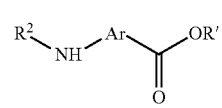

wherein $R^2$, Ar and R' are as defined in claim 28, said method comprising:

i) trifluoroacetylation of a 4-aminobenzoate of general formula $H_2N$—Ar—$CO_2R'$, to produce a trifluoroacetamidobenzoate ester of general formula: $F_3C$—C(=O)—NH—Ar—$CO_2R'$ where Ar and R' are as previously defined;

(ii) propargylation of said trifluoroacetamidobenzoate, to produce a (propargyl-trifluoroacetamido)benzoate of formula:

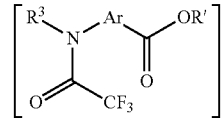

where $R^2$ is propargyl and Ar and R' are as previously defined; and (iii) hydrolysis of the product of step (iii) in situ to give the desired amine of formula

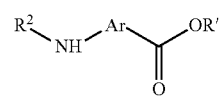

where $R^2$ is propargyl and Ar and R' are as previously defined.-

46. A process according to claim 1, wherein the cyclopentaquinazoline is a compound of general formula (VIII):

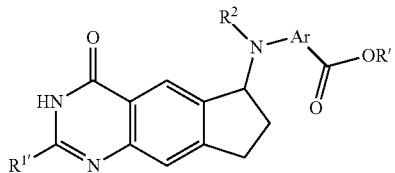

wherein $R^1$ is independently selected from hydrogen, amino, $C_{1-4}$alkyl, fluoro$C_{1-4}$alkyl, hydroxy$C_{1-4}$-alkyl, or protected hydroxy$C_{1-4}$-alkyl;
  $R^2$ is independently selected from hydrogen, $C_{1-4}$-alkyl, $C_{3-4}$alkenyl, $C_{3-4}$-alkynyl, hydroxy-$C_{2-4}$alkyl, halo$C_{2-4}$ alkyl or cyano$C_{1-4}$alkyl;
  Ar is independently selected from $C_{5-20}$ arylene, optionally substituted on the ring with one or two substituents selected from halogen, hydroxy, amino, nitro, cyano, trifluoromethyl, $C_{1-4}$alkyl and $C_{1-4}$alkoxy; and
  R' is hydrogen, or a protecting group.

47. A process according to claim 1, wherein the cyclopentaquinazoline is a compound of general formula (I):

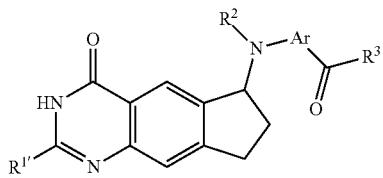

wherein R is independently selected from hydrogen, amino, $C_{1-4}$alkyl, $C_{1-4}$-alkoxy, fluoro$C_{1-4}$alkyl, hydroxy$C_{1-4}$-alkyl, or protected hydroxy$C_{1-4}$alkyl;
  $R^2$ is independently selected from hydrogen, $C_{1-4}$alkyl, $C_{3-4}$alkenyl, $C_{3-4}$alkynyl, hydroxy-$C_{2-4}$ alkyl, halo$C_{2-4}$ alkyl or cyano$C_{1-4}$alkyl;
  Ar is independently selected from $C_{5-20}$ arylene, optionally substituted on the ring with one or two substituents selected from halogeno, hydroxy, amino, nitro, cyano, trifluoromethyl, $C_{1-4}$ alkyl and $C_{1-4}$ alkoxy; and
  $R^3$ is a group of formula —NHCH($CO_2R''$)-$A^1$-$Y^1$ wherein $A^1$ is $C_{1-6}$ alkylene, R'' is hydrogen or a protecting group, and $Y^1$ is carboxy or a protected form thereof, tetrazol-5-yl, N—[$C_{1-4}$ alkylsulfonyl]carbamoyl, N-(phenylsulfonyl)carbamoyl, tetrazol-5-ylthio, tetrazol-5-ylsulfinyl or tetrazol-5-ylsulfonyl, wherein said
  N-(phenylsulfonyl)carbamoyl group may optionally bear one or two substituents on the phenyl ring selected from halogeno, nitro, $C_{1-4}$alkyl and $C_{1-4}$-alkoxy, or $Y^1$ is a group of the formula —CONH—CH($CO_2R''$)-$A^2$-$Y^2$ wherein the α-amino acid carbon atom has the D-configuration, $A^2$ is $C_{1-6}$alkylene and $Y^2$ is carboxy or a protected form thereof, or tetrazol-5-yl, wherein R'' is hydrogen or a protecting group,
  or $R^3$ is a N-linked naturally-occurring amino acid selected from the group consisting of L-alanine, L-leucine, L-isoleucine, L-valine and L-phenylalanine or a suitable carboxy-protected form thereof,
  or $R^3$ is a group of the formula —NH-$A^3$-$Y^3$ wherein $A^3$ is $C_{1-3}$alkylene and $Y^3$ is phenyl which may optionally bear one, two or three substituents selected from the group consisting of halogen, hydroxy, amino, nitro, cyano, trifluoromethyl, $C_{1-4}$alkyl and $C_{1-4}$alkoxy.

48. A process according to claim 47, wherein:
  $R^3$ is a group of formula —NHCH($CO_2H$)-$A^1$-$Y^1$ wherein $A^1$ is $C_{1-6}$alkylene and $Y^1$ is carboxy, tetrazol-5-yl, N—[$C_{1-4}$alkylsulfonyl]carbamoyl, N-(phenylsulfonyl)carbamoyl, tetrazol-5-ylthio, tetrazol-5-ylsulfinyl or tetrazol-5-ylsulfonyl, wherein said
  N-(phenylsulfonyl)carbamoyl group may optionally bear one or two substituents on the phenyl ring selected from halogen, nitro, $C_{1-4}$alkyl and $C_{1-4}$-alkoxy, or $Y^1$ is a group of the formula —CONH—CH($CO_2R''$)-$A^2$-$Y^2$ wherein the α-amino acid carbon atom has the D-configuration, $A^2$ is $C_{3-6}$alkylene and $Y^2$ is carboxy or tetrazol-5-yl,
  or $R^3$ is a N-linked naturally-occurring amino acid selected from the group consisting of L-alanine, L-leucine, L-isoleucine, L-valine and L-phenylalanine,
  or $R^3$ is a group of the formula —NH-$A^3$-$Y^3$ wherein $A^3$ is $C_{1-3}$alkylene and $Y^3$ is phenyl which may optionally bear one, two or three substituents selected from the group consisting of halogen, hydroxy, amino, nitro, cyano, trifluoromethyl, $C_{1-4}$alkyl and $C_{1-4}$alkoxy.

49. A process according to claim 1, wherein the cyclopentaquinazoline is a compound of general formula (VI):

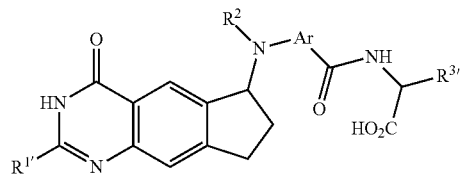

wherein $R^1$ is independently selected from hydrogen, amino, $C_{1-4}$-alkyl, $C_{1-4}$ alkoxy, fluoro$C_{1-4}$alkyl, hydroxy$C_{1-4}$-alkyl, or protected hydroxy$C_{1-4}$alkyl;
  $R^2$ is independently selected from hydrogen, $C_{1-4}$alkyl, $C_{3-4}$-alkenyl, $C_{3-4}$alkynyl, hydroxy-$C_{2-4}$-alkyl, halo$C_{2-4}$alkyl or cyano$C_{1-4}$alkyl;
  Ar is independently selected from $C_{5-20}$ arylene, optionally substituted on the ring with one or two substituents selected from halogeno, hydroxy, amino, nitro, cyano, trifluoromethyl, $C_{1-4}$ alkyl and $C_{1-4}$-alkoxy; and
  $R^{3'}$ is a group of formula: -$A^5$CON(R)CH($Y^4$)$Y^5$ in which $A^5$ is a $C_{1-6}$ alkylene group; R is hydrogen, $C_{1-4}$alkyl, $C_{3-4}$ alkenyl or $C_{3-4}$-alkynyl; $Y^4$ is carboxy or a protected form thereof, tetrazol-5-yl, N—($C_{1-4}$alkylsulfonyl)carbamoyl, N-(phenylsulfonyl)carbamoyl which may optionally bear one or two substituents on the phenyl ring selected from halogeno, nitro, $C_{1-4}$alkyl and $C_{1-4}$alkoxy, tetrazol-5-ylthio, tetrazol-5-ylsulfinyl or tetrazol-5-ylsulfonyl; and $Y^5$ is the side chain of a naturally occurring amino acid or a group of the formula: -$A^4$-$CO_2R''$ in which $A^4$ is $C_{1-6}$ alkylene and R'' is hydrogen or a protecting group.

50. A process according to claim 49, wherein $R^3$ is a group of formula: -$A^5$-CON(R)CH($Y^4$)$Y^5$ in which $A^5$ is a $C_{1-6}$ alkylene group; R is hydrogen, $C_{1-4}$alkyl, $C_{3-4}$alkenyl or $C_{3-4}$alkynyl; $Y^4$ is carboxy, tetrazol-5-yl, N—($C_{1-4}$alkylsulfonyl)carbamoyl, N-(phenylsulfonyl)carbamoyl which may optionally bear one or two substituents on the phenyl ring selected from halogen, nitro, $C_{1-4}$alkyl and $C_{1-4}$alkoxy, tetrazol-5-ylthio, tetrazol-5-ylsulfinyl or tetrazol-5-ylsulfonyl;

and $Y^5$ is the side chain of a naturally occurring amino acid or a group of the formula: $-A^4-CO_2H$ in which $A^4$ is $C_{1-6}$ alkylene.

51. A process according to claim 50, wherein $R^1$ is selected from optionally protected hydroxy$C_{1-4}$alkyl.

52. A process according to claim 51, wherein $R^1$ is hydroxymethyl or protected hydroxymethyl.

53. A process according to claim 52, wherein $R^2$ is independently $C_{3-4}$alkynyl.

54. A process according to claim 53, wherein $R^2$ is independently propargyl.

55. A process according to claim 54, wherein Ar is phenylene, optionally substituted on the ring with one or two substituents selected from halogeno, nitro, $C_{1-4}$alkyl and $C_{1-4}$alkoxy.

56. A process according to claim 55, wherein Ar is unsubstituted phenylene.

57. A process according to claim 49, wherein $R^3$ is a group of formula $-NHCH(CO^2H)R^{3'}$, wherein $R^{3'}$ is a group of formula: $-A^5-CON(R)CH(Y^4)Y^5$ in which $A^5$ is a $C_{1-6}$ alkylene group; R is hydrogen, $C_{1-4}$alkyl, $C_3$-4 alkenyl or $C_{3-4}$alkynyl;
  $Y^4$ is carboxy, tetrazol-5-yl, $N-(C_{1-4}$alkylsulfony carbamoyl, N-(phenylsulfonyl)carbamoyl which may optionally bear one or two substituents on the phenyl ring selected from halogen, nitro, $C_{1-4}$ alkyl and $C_{1-4}$-alkoxy, tetrazol-5-ylthio, tetrazol-5-ylsulfinyl or tetrazol-5-ylsulfonyl; and $Y^5$ is the side chain of a naturally occurring amino acid or a group of the formula: $-A^4$-$CO_2H$ in which $A^4$ is alkylene.

58. A process according to claim 49, wherein $R^{3'}$ is a group of formula: $-CH_2CH_2C(=O)NHCH(CO_2H)CH_2CH_2CH_2CO_2H$.

59. A process according to claim 49, wherein R' is a protecting group independently selected from $C_{1-4}$ alkyl, benzyl or allyl.

60. A process according to claim 59 wherein R' is a $C_{1-4}$ alkyl protecting group.

61. A process according to claim 1 wherein the 5-amino-6-haloindanone is a compound of general formula:

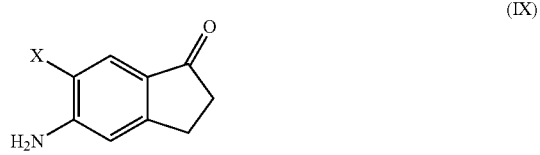

wherein X is a halide.

62. A process according to claim 1, wherein the cyclopentaquinazoline compound is (6RS)-4-(N-(2-{hydroxymethyl)-4-oxo-3,4,7,8-tetrahydro-3H-cyclopenta[g]quinazolin-6-yl)-N-(prop-2-ynyl)amino]benzoic acid.

63. A process according to claim 1, wherein the cyclopentaquinazoline compound is (6S)-4-(N-(2-(hydroxymethyl)-4-oxo-3,4,7,8-tetrahydro-3H-cyclopenta[g]quinazolin-6-yl)-N-(prop-2-ynyl)amino]benzoic acid.

64. A process according to claim 1, wherein the cyclopentaquinazoline compound is N-{N-{4N-((6S)-2-hydroxymethyl-4-oxo-3,4,7,8-tetrahydro-6H-cyclopenta[g]quinazolin-6-yl)-N-(prop-2-ynyl)amino]benzoyl}-L-γ-glutamyl}-D-glutamic acid (ONX-0801):

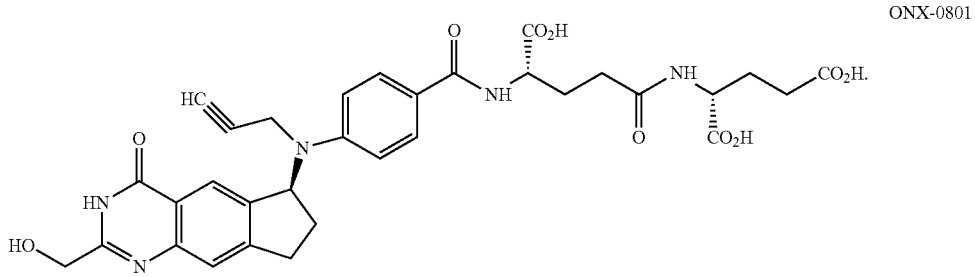 [SMILES: C#CCN(c1ccc(C(=O)N[C@@H](CCC(=O)N[C@H](CCC(=O)O)C(=O)O)C(=O)O)cc1)[C@H]1CCc2cc3nc(CO)[nH]c(=O)c3cc21]

ONX-0801

65. A compound, useful in the method of claim 1, selected from:
  5-(t-butoxyacetamido)-6-bromoindan-1-one;
  5-(benzyloxyacetamido)-6-cyanoindan-1-one;
  5-(t-butoxyacetamido)-6-cyanoindan-1-one;
  6-aminocarbonyl-5-(benzyloxyacetamido)indan-1-one;
  6-amino carbonyl-5-(t-butoxyacetamido)indan-1-one;
  2-(benzylyoxymethyl)-4,6-dioxo-3,4,7,8-tetrahydro-3H-cyclopenta[g]quinazoline;
  2-(hydroxymethyl)-4,6-dioxo-3,4,7,8-tetrahydro-3H-cyclopenta[g]quinazoline;
  2-(t-butoxymethyl)-4,6-dioxo-3,4,7,8-tetrahydro-3H-cyclopenta[g]quinazoline;
  2-(t-butyldimethylsiloxymethyl)-4,6-dioxo-3,4,7,8-tetrahydro-3H-cyclopenta[g]quinazoline;
  (R,S)-2-(t-butyldimethylsiloxymethyl)-6-hydroxy-4-oxo-3,4,7,8-tetrahydro-3H-cyclopenta[g]quinazoline;
  (R)-2-(t-butyldimethylsiloxymethyl)-6-hydroxy-4-oxo-3,4,7,8-tetrahydro-3H-cyclopenta[g]quinazoline;
  (S)-2-(t-butyldimethylsiloxymethyl)-6-hydroxy-4-oxo-3,4,7,8-tetrahydro-3H-cyclopenta[g]quinazoline;
  (R,S)-2-(t-butoxymethyl)-6-hydroxy-4-oxo-3,4,7,8-tetrahydro-3H-cyclopenta[g]quinazoline;
  (R)-2-(t-butoxymethyl)-6-hydroxy-4-oxo-3,4,7,8-tetrahydro-3H-cyclopenta[g]quinazoline;
  (S)-2-(t-butoxymethyl)-6-hydroxy-4-oxo-3,4,7,8-tetrahydro-3H-cyclopenta[g]quinazoline;
  t-butyl (6RS)-4,N-((2-(t-butyldimethylsiloxymethyl)-4-oxo-3,4,7,8-tetrahydro-3H-cyclopenta[g]quinazolin-6-A-N-(prop-2-ynyl)amino)benzoate;
  t-butyl (6S)-4,N-((2-{t-butyldimethylsiloxymethyl)-4-oxo-3,4,7,8-tetrahydro-3H-cyclopenta[g]quinazolin-6-yl)-N-(prop-2-ynyl)amino)benzoate;
  t-butyl (6R)-4,N-(t-butyldimethylsiloxymethyl)-4-oxo-3,4,7,8-tetrahydro-3H-cyclopenta[g]quinazolin-6-yl)-N-(prop-2-ynyl)amino)benzoate;
  t-butyl (6RS)-4,N-((2-(t-butoxymethyl)-4-oxo-3,4,7,8-tetrahydro-3H-cyclopenta[g]quinazolin-6-yl)-N-(prop-2-ynyl)amino)benzoate;
  t-butyl (6S)-4,N-(2-(t-butoxymethyl)-4-oxo-3,4,7,8-tetrahydro-3H-cyclopenta[g]quinazolin-6-yl)-N-(prop-2-ynyl)amino)benzoate; and t-butyl (6R)-4,N-(2-(t-butoxymethyl)-4-oxo-3,4,7,8-tetrahydro-3H-cyclopenta[g]quinazolin-6-yl)-N-(prop-2-ynyl)amino)benzoate.

66. A method of synthesizing a cyclopentaquinazoline, comprising a step involving reaction of a compound according to claim 65, or a compound selected from (6S)-4,N-((2-(hydroxymethyl)-4-oxo-3,4,7,8-tetrahydro-3H-cyclopenta[g]quinazolin-6-yl)-N-(prop-2-ynyl)amino)benzoic acid;

(6S)-4,N-((2-(hydroxymethyl)-4-oxo-3,4,7,8-tetrahydro-3H-cyclopenta[g]quinazolin-6-yl)-N-(prop-2-ynyl)amino)benzoic acid; and (6RS)-4,N((2-(hydroxymethyl)-4-oxo-3,4,7,8-tetrahydro-3H-cyclopenta[g]quinazolin-6-yl)-N-(prop-2-ynyl)amino)benzoic acid.

* * * * *